(12) United States Patent
Bloch et al.

(10) Patent No.: US 6,601,580 B1
(45) Date of Patent: Aug. 5, 2003

(54) ENHANCING THERAPEUTIC EFFECTIVENESS OF NITRIC OXIDE INHALATION

(75) Inventors: Kenneth D. Bloch, Brookline, MA (US); Fumito Ichinose, Brookline, MA (US); Warren M. Zapol, Concord, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/605,900

(22) Filed: Jun. 28, 2000

(51) Int. Cl.[7] ...................... A61M 11/00; A61M 15/00; A61M 16/00
(52) U.S. Cl. ........................... 128/200.14; 128/200.24; 128/203.15
(58) Field of Search .......................... 28/200.14, 200.23, 28/203.15, 200.24; 514/929

(56) References Cited

U.S. PATENT DOCUMENTS

| | | | |
|---|---|---|---|
| 5,396,882 A | 3/1995 | Zapol |
| 5,427,797 A | 6/1995 | Frostell et al. |
| 5,485,827 A | 1/1996 | Zapol et al. |
| 5,570,683 A | 11/1996 | Zapol |
| 5,728,705 A | 3/1998 | Lawson et al. |
| 5,823,180 A | 10/1998 | Zapol |
| 5,885,621 A | 3/1999 | Head et al. |
| 6,063,407 A | 5/2000 | Zapol et al. |

FOREIGN PATENT DOCUMENTS

EP    0 692 984 B1    1/1996

OTHER PUBLICATIONS

Jones et al. Pharmacology of the Leukotriene Antagonist Verlukast: The (R)–Enantiomer of MK–571; Can. J. Physiol. Pharmacol., 1991, 69(12); PubMed Abstract.*

Kusner et al. The 5–Lipoxygenase Inhibitors ZD2138 and ZM230487 are Potent And Selective Inhibitors of Several Antigen–Induced Guinea–Pig Pulmonary Responses; Eur. J. Pharmacol., 1994, 257(3); PubMed Abstract.*

Baker et al. Synthetic Combined Superoxide Dismutast/Catalase Mimetics are Protective as a Delayed Treatment in a Rat Stroke Model: A Key Role for Reactive Oxygen Species in Ischemic Brain Injury; Journal of Pharm. and Exper. Thera., 1998, vol. 284, No. 1.*

Charleson et al. Structural Requirements for the Binding of Fatty Acids to 5–Lipoxygenase–Activating Protein; Eur. J. Pharmacol., 1994, 17; 267 (3): PubMed Abstract.*

Gauthier et al. Stereospecific Synthesis, Assignment of Absolute Configuration, and Biological Activity of the Enantiomers of 3–[[[3–[2–(7–3–Chloroquinolin–2–YL)–e)–Ethenyl]Phenyl]] [[3–(Dimethylamino)–3–Oxopropyl]Thio . . . ; J.Med.Chem., 1990 (10); PubMed.*

Hatzelmann et al. Mode of Action of the New Selective Leukotriene Synthesis Inhibitor Gay X 1005 ((R–2–[4–9Quinolin–2–YL–Methoxy)Phenyl]–2–Cyclopentyl Acetic Acid) and Structurally Related Compounds; Biochem. Pharmacol., 1993, 45(1): PubMed Abstract.*

Bigatello et al., "Prolonged Inhalation of Low Concentrations of Nitric Oxide in Patients with Severe Adult Respiratory Distress Syndrome," Anesthesiology 80:761–770 (1994).

Dellinger et al., "Effects of Inhaled Nitric Oxide in Patients with Acute Respiratory Distress Syndrome: Results of a Randomized Phase II Trial," Crit. Care Med. 26: 15–23 (1998).

Frostell et al., "Inhaled Nitric Oxide, A Selective Pulmonary Vasodilator Reversing Hypoxic Pulmonary Vasoconstriction," Circulation 83:2038–2047 (1991).

Gerlach et al., "Low Levels of Inhaled Nitric Oxide in Acute Lung Injury," Nitric Oxide and the Lung (Zapol and Block, eds.), Marcel Dekker Inc., New York, 271–283.

Holzmann et al., "Hyporesponsiveness to Inhaled Nitric Oxide in Isolated, Perfused Lungs from Endotoxin–Challenged Rats," American Journal of Physiology 271:L981–L986 (1996).

Holzmann et al., "Inhibition of Nitric–Oxide Synthase Prevents Hyporesponsiveness to Inhaled Nitric Oxide in Lungs from Endotoxin–Challenged Rats," Anesthesiology 91:215–221 (1999).

Hutchinson et al., "Effect of Endotoxemia on Hypoxic Pulmonary Vasoconstriction in Unanesthetized Sheep," J. Appl. Physiol. 58: 1463–1468 (1985).

Ichinose et al., "Preserved Hypoxic Polmonary Vasoconstriction in 5–Lypoxygenase Deficient Mice," Am. J. Respiratory and Critical Care Medicine 161:A411 (abstr.).

Krafft et al., "Effectiveness of Nitric Oxide Inhalation in Septic ARDS," Chest 109:486–493 (1996).

Manktelow et al., "Physiologic Determinants of the Response to Inhaled Nitric Oxide in Patients with Acute Respiratory Distress Syndrome," Anesthesiology 87:297–307.

(List continued on next page.)

Primary Examiner—Jon P. Weber
Assistant Examiner—Patricia A Patten
(74) Attorney, Agent, or Firm—Fish & Richardson P.C.

(57) ABSTRACT

Methods for reducing, partially preventing or completely preventing nitric oxide (NO) inhalation-related impairment of HPV in a mammal are disclosed. The methods include administering a therapeutically effective amount of NO by inhalation, and co-administering an effective amount of an anti-reactive oxygen species (anti-ROS) agent, e.g., N-acetylcysteine, or a leukotriene blocker. Methods for reducing, partially preventing or completely preventing loss of pulmonary vasodilatory responsiveness to NO inhalation in a mammal are also disclosed. The methods include administering a therapeutically effective amount of NO by inhalation, and co-administering an effective amount of an anti-ROS agent a therapeutically effective amount of a leukotriene blocker.

36 Claims, 13 Drawing Sheets

OTHER PUBLICATIONS

Panin et al., "The Role of Hepatocytes and Kupffer's and Endothelial Liver Cells in Blood Lipoprotein Metabolism," *Biochemistry (Moscow)* 59:249–254.

Raveh et al., 1999, *Anesthesiology* 91 (supplement): Abstract No. A713.

Rossaint et al., "Inhaled Nitric Oxide for the Adult Respiratory Distress Syndrome," *New England Journal of Medicine* 328:399–405 (1993).

Ullrich et al., "Hypoxic Pulmonary Blood Flow Redistribution and Arterial Oxygenation in Endotoxin–Challenged NOS2–Deficient Mice," *J. Clin. Invest.* 104:1421–1429 (1999).

Ullrich et al., "N–Acetylcysteine Partially Preserves Hypoxic Pulmonary Vasoconstriction (HPV) in Endotoxin Challenged Mice," *Am. J. Respiratory and Critical Care Medicine* 161:A628 (abstr.).

Weimann et al., "Congenital NOS2 Deficiency Protects Mice from LPS–Induced Hyporesponsiveness to Inhaled Nitric Oxide," *Anesthesiology* 91:1744–1753 (1999).

Xia et al., "Superoxide and Peroxynitrite Generation from Inducible Nitric Oxide Synthase in Macrophages," *Proc. Natl. Acad. Sci* 94:6954–6958 (1997).

Foubert, et al., "Safety Guidelines for use of Nitric Oxide", *The Lancet*, 339: 1615–1616 (1992).

Groves, et al., "Exogenous Nitric Oxide Inhibits in Vivo Platelet Adhesion Following Balloon Angioplasty" *Cardiovasc Res* 26(6): 615–9 (Jun. 1992).

Högman, et al., "Prolonged Bleeding Time During Nitric Oxide Inhalation in the Rabbit", *Acta Physiol. Scand* 151: 125–129 (1994).

Ignarro, L.J., "Endothelium–Derived Nitric Oxide: Actions and Properties", *The FASEB Journal* 3 : 31–36 (1989).

Ignarro, L.J., "Endothelium–Derived Nitric Oxide: Pharmacology and Relationship to the Actions of Organic Nitrate Esters", *Pharmaceutical Research* 6: 8 651–659 (1989).

Radomski, et al., "The Anti–Aggregating Properties of Vascular Endothelium: Interactions Between Prostacyclin and Nitric Oxide", *Br. J. Pharmac.* 92: 639–646 1987).

Sellden, et al., "Inhalation of Nitric Oxide Reduced Pulmonary Hypertension After Cardiac Surgery in a 3.2–kg Infant", *Anesthesiology* 78(3): 577–80 (Mar., 1993).

Stamler, et al., "S–Nitrosylation of Proteins with Nitric Oxide: Synthesis and Characterization of Biologically Active Compounds" *Proc. Natl. Acad. Sci, USA* 89: 444–448 (Jan. 1992).

* cited by examiner

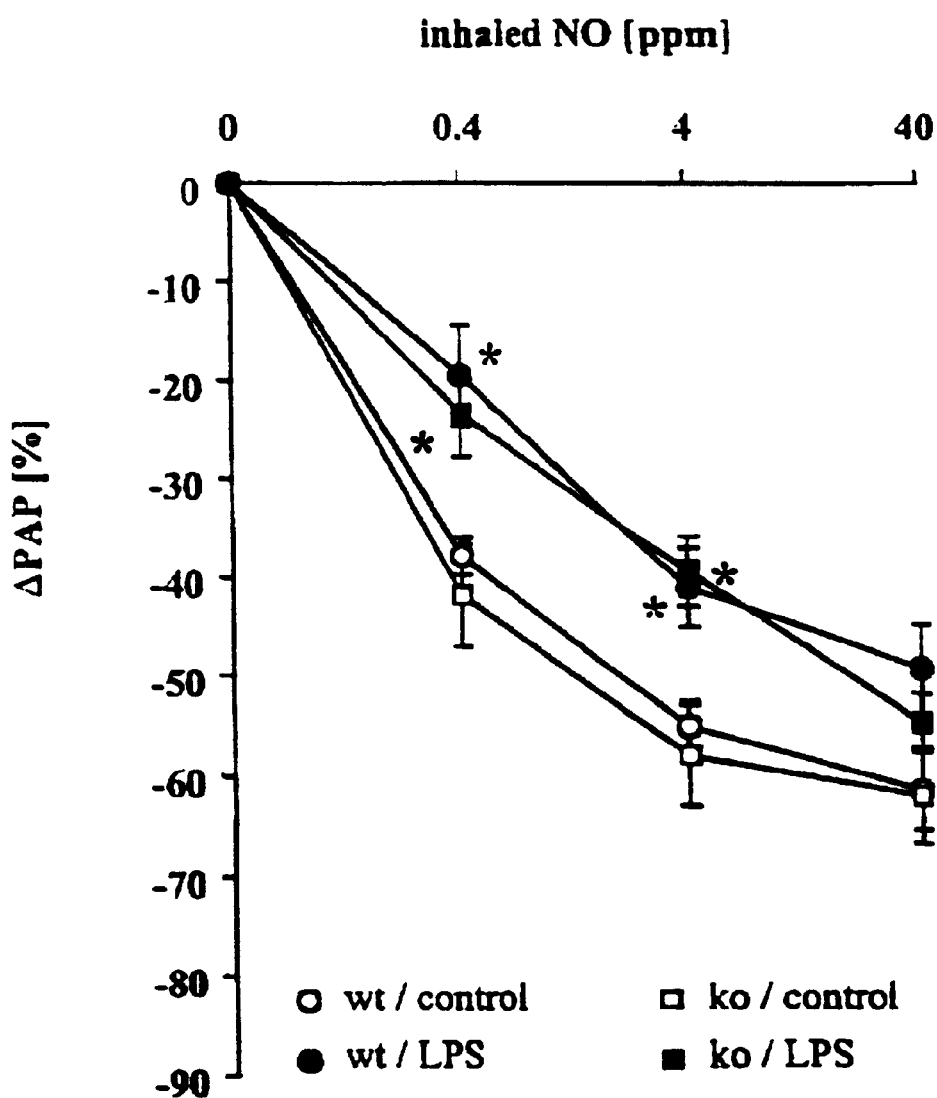

FIG. 12

| | | NOS2+/+ Control | NOS2-/- Control | NOS2+/+ Endotoxin | NOS2-/- Endotoxin | NOS2+/+ Control +40 ppm NO | NOS2-/- Control +40 ppm NO | NOS2+/+ Endotoxin +40 ppm NO | NOS2-/- Endotoxin +40 ppm NO |
|---|---|---|---|---|---|---|---|---|---|
| N | | 7 | 7 | 6 | 6 | 5 | 5 | 5 | 5 |
| HR (beats per minute) | Baseline | 394 ± 15 | 423 ± 21 | 338 ± 13 | 374 ± 17 | 412 ± 18 | 450 ± 27 | 348 ± 27 | 398 ± 25 |
| | LMBO | 394 ± 21 | 446 ± 34 | 347 ± 32 | 372 ± 23 | 412 ± 21 | 438 ± 25 | 343 ± 24 | 441 ± 18 |
| $P_{SA}$ (mmHg) | Baseline | 113 ± 5 | 107 ± 11 | 100 ± 4 | 103 ± 5 | 97 ± 13 | 105 ± 16 | 97 ± 7 | 113 ± 4 |
| | LMBO | 80 ± 17[B] | 94 ± 12 | 92 ± 8 | 87 ± 5 | 103 ± 7 | 100 ± 20 | 88 ± 6 | 104 ± 9 |
| $P_{PA}$ (mmHg) | Baseline | 15 ± 2 | 15 ± 1 | 16 ± 2 | 14 ± 1 | 15 ± 3 | 15 ± 3 | 21 ± 3 | 19 ± 1 |
| | LMBO | 16 ± 2 | 16 ± 1 | 17 ± 2 | 15 ± 2 | 16 ± 2 | 18 ± 3 | 21 ± 3 | 16 ± 1 |
| QPA (µL/min per g bw) | Baseline | 200 ± 32 | 160 ± 9 | 230 ± 35 | 120 ± 32 | 140 ± 19 | 130 ± 24 | 200 ± 59 | 170 ± 17 |
| | LMBO | 170 ± 23 | 150 ± 1 | 210 ± 29 | 130 ± 4 | 150 ± 33 | 130 ± 32 | 180 ± 47 | 190 ± 32 |
| QRPA (µL/min per gram bw) | Baseline | 130 ± 18 | 90 ± 5 | 150 ± 20 | 80 ± 26 | 80 ± 7 | 80 ± 18 | 130 ± 37 | 110 ± 10 |
| | LMBO | 140 ± 19 | 120 ± 8[A] | 150 ± 21 | 110 ± 39[A] | 130 ± 18[C] | 110 ± 27[A] | 130 ± 35 | 140 ± 28[A] |
| QLPA (µL/min per gram bw) | Baseline | 80 ± 15 | 60 ± 6 | 80 ± 16 | 50 ± 7 | 50 ± 12 | 50 ± 8 | 70 ± 22 | 60 ± 8 |
| | LMBO | 30 ± 5[C] | 30 ± 4[C] | 60 ± 11 | 20 ± 3[A] | 30 ± 11[A] | 30 ± 8[A] | 50 ± 12 | 50 ± 6 |
| QLPA/QPA (%) | Baseline | 36 ± 3 | 40 ± 2 | 35 ± 2 | 42 ± 4 | 36 ± 4 | 41 ± 4 | 36 ± 4 | 36 ± 2 |
| | LMBO | 19 ± 2[C] | 20 ± 2[B] | 29 ± 3 | 21 ± 3[B] | 18 ± 5[B] | 20 ± 4[B] | 28 ± 2[A] | 29 ± 2[A] |

ENHANCING THERAPEUTIC EFFECTIVENESS OF NITRIC OXIDE INHALATION

TECHNICAL FIELD

This invention relates to pulmonary physiology and cardiology.

BACKGROUND

Nitric oxide (NO) is a highly reactive free radical compound produced by many cells of the body. It relaxes vascular smooth muscle by binding to the heme moiety of cytosolic guanylate cyclase, activating guanylate cyclase and increasing intracellular levels of cyclic guanosine 3',5'-monophosphate (cGMP), leading to vasodilation.

When inhaled, NO gas acts as a selective vasodilator of human and animal pulmonary vessels. Consequently, NO inhalation is used to promote vasodilation in well-ventilated regions of the lung. In acute respiratory distress syndrome (ARDS), impaired ventilation of lung tissue reduces oxygenation of arterial blood. Nitric oxide inhalation often improves oxygenation in ARDS patients. It does so by dilating blood vessels in well-ventilated portions of the lung, redistributing blood flow towards the well-ventilated regions and away from poorly-ventilated regions, which receive little NO. However, in 30–40% of ARDS patients, NO inhalation fails to improve arterial oxygenation (Bigatello et al., 1994, *Anesthesiology* 80:761–770; Dellinger et al., 1998, *Crit. Care Med.* 26:15–23). It is difficult to predict which patients with ARDS will not respond to NO inhalation or which patients will respond only transiently. However, it is known that up to 60% of patients with ARDS associated with sepsis do not respond to inhaled NO (Krafft et al., 1996, *Chest* 109:486–493).

Normal pulmonary vasculature constricts in response to alveolar hypoxia. In patients with lung injury such as ARDS, hypoxic pulmonary vasoconstriction (HPV) raises the level of systemic arterial oxygenation by redistributing blood flow away from a poorly ventilated (hypoxic) lung or lung region toward a well-ventilated (normoxic) lung regions. Sepsis and endotoxemia impair HPV (Hutchinson et al., 1985, *J. Appl. Physiol.* 58:1463–1468) leading to a profound decrease in arterial oxygen concentrations. Such a decreased level of systemic oxygenation can be life-threatening. Nitric oxide inhalation might be expected to improve oxygenation or arterial blood during sepsis, by increasing blood flow in well-ventilated regions on the lung. In practice, however, NO inhalation during sepsis is often ineffective, and sometimes is deleterious, because of NO inhalation-related reduction of HPV. See, e.g., Gerlach et aL., 1996, "Low levels of inhaled nitric oxide in acute lung injury," pages 271–283 in *Nitric Oxide and the Lung*, (Zapol and Bloch, eds.), Marcel Dekker Inc, New York.

Endogenous NO is produced by nitric oxide synthases through conversion of L-arginine to L-citrulline in the presence of oxygen (Knowles et al., 1994, *Biochemistry* 298:249–258). Three different forms of nitric oxide synthase (NOS) have been characterized. Neuronal NOS (NOS1) and endothelial NOS (NOS3) are constitutive enzymes. An inducible NOS known as NOS2 capable of producing large amounts of NO is induced by endotoxin (also referred to as lipopolysaccharide or LPS) and cytokines (Knowles et al., supra). In spite of the demonstrated value of NO inhalation therapy for various indications, impaired pulmonary vascular dilatory responsiveness to NO inhalation and NO-related loss of HPV remain significant problems in acute respiratory illness.

SUMMARY

The inventors have discovered that an increased pulmonary NO level is necessary to to impair HPV during sepsis, and that such HPV impairment can be ameliorated by reactive oxygen species scavengers or leukotriene blockers. Accordingly, the inventors have developed methods for preserving the vasodilatory effect of NO inhalation to achieve improved arterial blood oxygenation in patients with lung injury, while ameliorating HPV-reducing effects of NO inhalation. The inventors have discovered that the impairment of HPV is not simply NO-mediated vasodilation. The inventors also have discovered that an elevated level of pulmonary NO plus other lipopolysaccharide-induced agents are necessary to impair pulmonary vasodilatory responsiveness to NO inhalation in endotoxin-challenged mice. Accordingly, the inventors have developed methods for preserving pulmonary vasodilator responsiveness to NO inhalation.

In one aspect, the invention features a method for reducing, partially preventing or completely preventing NO inhalation-related impairment of HPV in a mammal. In one embodiment, the method includes administering to the mammal a therapeutically effective amount of NO by inhalation, and co-administering an effective amount of an anti-reactive oxygen species (anti-ROS) agent. The anti-ROS agent can be, e.g., N-acetylcysteine, allopurinol, ascorbic acid (vitamin C), bilirubin, caffeic acid, catalase, PEG-catalase, ceruloplasm, copper diisopropylsalicylate, deferoxamine mesylate, dimethylurea, ebselen (2-phenyl-1, 2-benzisoselenazol-3(2H)-one; Pz51), EUK-8, FeTMTPyP (5, 10, 15, 20-tetrakis(N-methyl-4'-pyridyl)porphinato iron (III) chloride), FETPPS (5, 10, 15, 20-tetrakis(4-sulfonatophenyl)porphyrinato iron (III) chloride), glucocorticoids, glutathione, MnTBAP (Mn(III)tetrakis(4-benzoic acid)porphyrin chloride), MnTMPyP (Mn(III) tetrakis(1-methyl-4-pyridyl)porphyrin pentachloride), selenomethionine, superoxide dismutase (SOD), polyethylene glycol-conjugated-SOD (PEG-SOD), Taxifolin (dihydroquercetin; 3,3',4',5,7-pentahydroxyflavone), and vitamin E. N-acetylcysteine is a preferred anti-ROS agent. In alternative embodiment, the method includes administering a therapeutically effective amount of NO by inhalation, and co-administering an effective amount of a leukotriene blocker. In other embodiments, two or more anti-ROS agents, or an anti-ROS agent and a leukotriene blocker are co-administered with NO inhalation.

In another aspect, the invention features methods for reducing, partially preventing or completely preventing loss of pulmonary vasodilatory responsiveness to NO inhalation in a mammal. In one embodiment, the method includes administering to the mammal a therapeutically effective amount of NO by inhalation, and co-administering an effective amount of an anti-ROS agent. In alternative embodiment, the method includes administering a therapeutically effective amount of NO by inhalation, and co-administering an effective amount of a leukotriene blocker. In other embodiments, two or more anti-ROS agents, or an anti-ROS agent and a leukotriene blocker are co-administered with NO inhalation.

Unless otherwise defined, all technical and scientific terms used herein have the same meaning as commonly understood by a person of ordinary skill in the art to which the invention belongs. In case of conflict, the present application, including definitions, will control. All publications, patents, and other documents mentioned herein are incorporated by reference.

Although methods and materials similar or equivalent to those described herein can be used in the practice or testing of the invention, the preferred methods and materials are described below. The materials, methods and examples are illustrative only and not intended to be limiting. Other features and advantages of the invention will be apparent from the detailed description and from the claims.

DESCRIPTION OF DRAWINGS

FIG. 3 is a graph summarizing data on vasodilation by short term NO inhalation in isolated-perfused lungs from lipopolysaccharide-pretreated (wild-type/LPS) and untreated (wild-type/control) wild-type mice, and in isolated-perfused lungs from lipopolysaccharide-pretreated (ko/LPS) and untreated (ko/control) NOS2-deficient mice previously exposed to 20 ppm NO for 16 hours in ambient air. After prolonged NO exposure, lipopolysaccharide-pretreated NOS2 deficient mice were less responsive to short-term NO inhalation than were NOS2-deficient mice that did not receive lipopolysaccharide (*$P<0.05$). Similarly, after prolonged NO exposure, lipopolysaccharide-pretreated wild-type mice were less responsive to short-term NO inhalation than were wild-type mice that did not receive lipopolysaccharide (*$P<0.05$). Data are expressed as mean±SE.

FIG. 12 is a table of data from hemodynamic measurements. Hemodynamic measurements were before LMBO (baseline) and 5 minutes after left lung hypoxia (LMBO) in wild-type mice (NOS2 +/+) and NOS2-deficient mice (NOS2 −/−) challenged with saline (control) or endotoxin (endotoxin) 22 hours before hemodynamic experiments, and with and without inhalation of 40 ppm NO in air for 22 hours (as measured 1 hour after discontinuation of NO inhalation). HR=heart rate ($min^{-1}$), PSA=mean systemic arterial pressure (mmHg), $P_{PA}$=mean pulmonary artery pressure (mmHg), QPA=flow through right pulmonary artery during left pulmonary artery occlusion ($\mu l \times min^{-1} \times g^{-1} bw$), $Q_{RPA}$= flow through right pulmonary artery ($\mu l \times min^{-1} \times g^{-1} bw$), $Q_{LPA}$=flow through left pulmonary artery ($\mu l \times min^{-1} g^{-1} bw$), $Q_{LPA}/Q_{PA}$=ratio of flow through left pulmonary artery to flow through right pulmonary artery during transient left pulmonary artery occlusion. All values at baseline before LMBO were compared between groups by ANOVA. The effect of LMBO on each parameter was analyzed in each group by ANOVA with a post hoc comparison ($^AP<0.05$, $^BP<0.01$, $^CP<0.001$ versus baseline).

DETAILED DESCRIPTION

NO Inhalation

Figure 1:
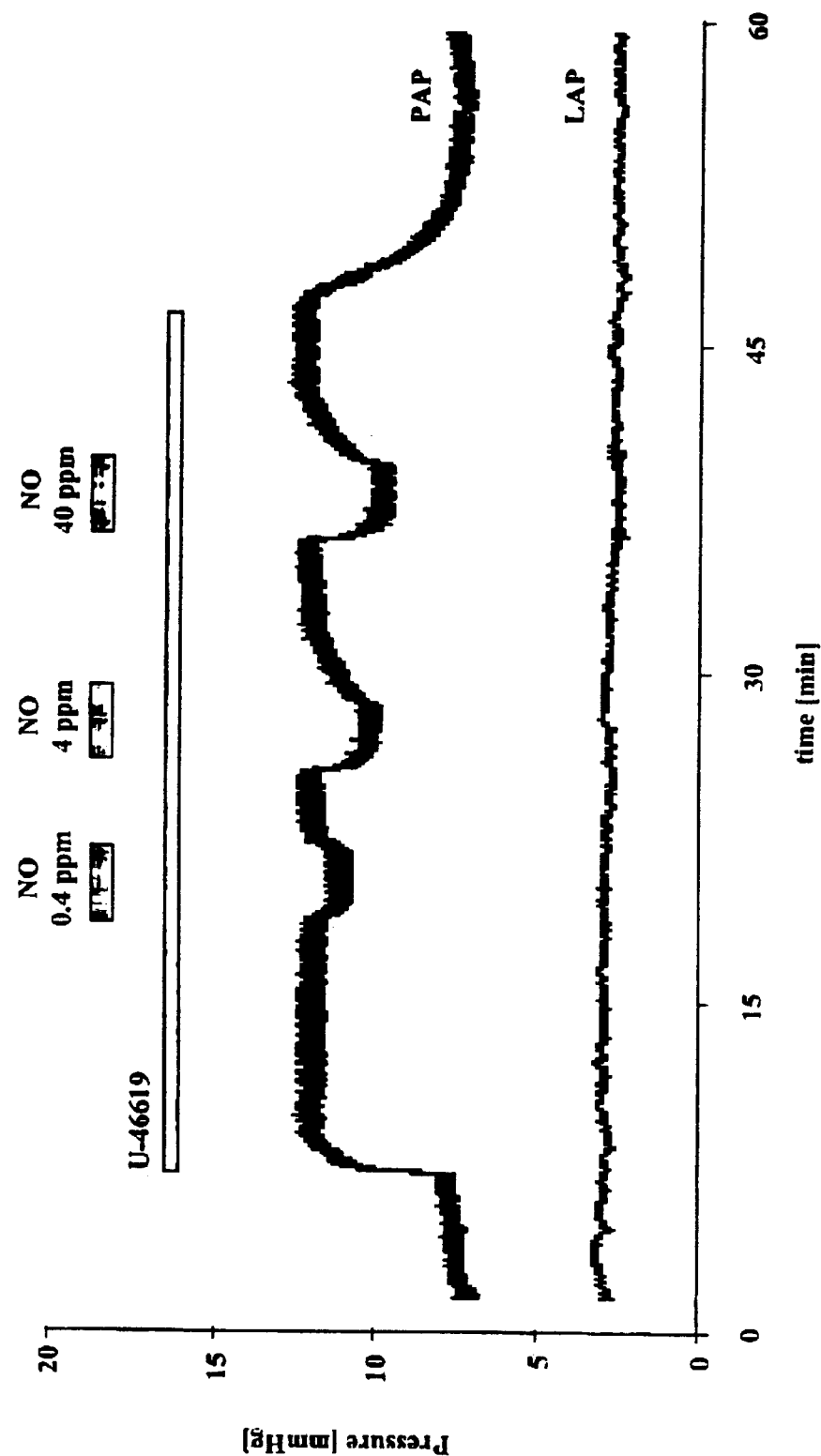
FIG. 1 is a tracing from a representative experiment measuring pulmonary artery pressure (PAP; equivalent to perfusion pressure) and left atrial pressure (LAP) in an isolated-perfused lung of an untreated wild-type mouse. The stable thromboxane $A_2$ analog U46619 was infused to increase PAP by 5 or 6 mmHg. Varying doses (0.4, 4.0, and 40 ppm) of NO gas were administered for 5 minutes each. After each dose, PAP was allowed to return to the pre-NO level.

Methods for safe and effective administration of NO by inhalation are well known in the art. See, e.g., Zapol, U.S. Pat. No. 5,570,683; Zapol et al., U.S. Pat. No. 5,904,938; Frostell et al., 1991, *Circulation* 83:2038–2047. NO for inhalation is available commercially (INOmax™, INO Therapeutics, Inc., Clinton, N.J.). In the present invention, NO inhalation preferably is in accordance with established medical practice.

A suitable starting dosage for NO administered by inhalation is 20 ppm. See, e.g., INOmax™ package insert (www.inotherapeutics.com). However, dosage can vary, e.g., from 0.1 ppm to 100 ppm, depending on the age and condition of the patient, the disease or disorder being treated, and other factors that the treating physician may deem relevant. Preferably, the lowest effective dose is inhaled. To arrive at the lowest effective dosage empirically, administration can be commenced at 20 ppm and then decreased gradually until vasodilator efficacy is lost. Where 20 ppm is deemed an insufficient inhaled dose, NO dosage may be increased gradually until vasodilator effectiveness is observed. Such adjustment of dosage is routine for those of skill in the art. An advantage of the present invention is that in many cases it enables achievement of a desired therapeutic outcome at an NO dosage lower than that required if NO were administered alone. In addition, it may allow for an inhaled NO response where none would occur otherwise, e.g., with septic lung injury, or it may allow preservation of the response despite the progress of acute lung injury.

Anti-ROS Agent

Reactive oxygen species (ROS) include the superoxide radical ($O_2^\bullet$), hydrogen peroxide ($H_2O_2$), and the hydroxyl radical (OH•). As used herein, "anti-ROS agent" means a compound that: (1) inhibits production of reactive oxygen species; or (2) scavenges, i.e., rapidly reacts with, reactive oxygen species, once produced. Numerous anti-ROS agents useful in the present invention are known. Examples of anti-ROS agents include: N-acetylcysteine (Mucosil™), allopurinol, ascorbic acid (vitamin C), bilirubin, caffeic acid, catalase, PEG-catalase, catechin, ceruloplasm, copper diisopropylsalicylate, deferoxamine mesylate, dimethylurea, ebselen, EUK-8, FeTMTPyP, FETPPS, glucocorticoids, glutathione, MnTBAP, MnTMPyP, selenomethionine, superoxide dismutase, PEG-superoxide dismutase, Taxifolin, and vitamin E. In some embodiments of the invention, two or more anti-ROS agents are employed in combination. A preferred anti-ROS agents is N-acetylcysteine (MUCOSIL™, Dey, Napa, Calif.), which is commercially available in sterile solution (10% or 20%) suitable for inhalation as an aerosol mist, e.g., using a conventional nebulizer.

Some anti-ROS agents also scavenge peroxynitrite, a toxic reactive nitrogen species produced by the reaction of NO with superoxide. Scavenging reactive nitrogen species may reduce, partially prevent or completely prevent NO inhalation-related impairment of HPV and loss of pulmonary vasodilatory responsiveness to NO inhalation.

Dosage and route of administration of the anti-ROS agent(s) will depend on the particular agent(s) employed. Safe and effective dosages and routes of administration for the various anti-ROS agents are known in the art. See, e.g., *Physician's Desk Reference* (PDR®), *Clinical Pharmacology* 2000, Gold Standard Multimedia (http://cp.gsm.com/fromcpo.asp), or vendor's package inserts.

A preferred anti-ROS agent is N-acetylcysteine, available commercially as MUCOMYST™, MUCOSIL-10™, and MUCOSIL-20™. Suitable routes of administration for N-acetylcysteine include oral, rectal, nebulized aerosol, and intravenous. Ultrasonic or conventional nebulizers may be used to administer N-acetylcysteine. (Because N-acetylcysteine reacts with certain materials, e.g., iron, copper, and rubber, any part of the nebulizer equipment that comes in contact with N-acetylcysteine should be made of plastic or glass.) Exemplary dosage regimens for N-acetylcysteine (MUCOSIL™) include, but are not limited to, the following:

20-hour IV regimen: 150 mg/kg IV (diluted in 200 ml of D5W) over 15 minutes, followed by 50 mg/kg IV (diluted in 500 ml of D5W) over 4 hours, then 100 mg/kg IV (diluted in 1000 ml of D5W) over 16 hours. 48-hour IV regimen: 140 mg/kg IV (diluted in 1:5 in D5W) over 1 hour, followed four hours after initiation of the loading dose by the first of 12 doses of 70 mg/kg IV (diluted 1:5 in D5W) every 4 hours for a total dose of 980 mg/kg. Each dose of the 48 hour regimen is given IV over 1 hour.

Nebulization using face mask, mouth piece or tracheostomy: Adults and adolescents: 5–10 ml of 20% solution, or 10–20 ml of the 10% solution every 6–8 hours. Children: 3–5 ml of 20% solution, or 6–10 ml of the 10% solution every 6–8 hours. Infants: 1–2 ml of 20% solution, or 2–4 ml of the 10% solution every 6–8 hours.

Nebulization using tent or croupette: Adults and children: A sufficient volume of 10% or 20% solution to provide a heavy mist, up to 300 ml may be required.

Oral or rectal dosage for children: 5–30 ml of the 10% solution given 3–6 times per day, e.g., 10 ml four times per day.

Preferably, administration of the anti-ROS agent is commenced concurrently with NO inhalation initiation. Duration of anti-ROS agent administration will depend on the agent employed and duration of the NO inhalation.

Leukotriene Blocker

Leukotrienes are a class of biologically active compounds that occur naturally in leukocytes. Leukotrienes produce allergic and inflammatory reactions similar to those of histamine. Arachidonic acid is converted to leukotriene A4 by the action of 5-lipoxygenase (5LO) and the 5LO-activating protein (FLAP). Leukotriene A4 is rapidly converted to leukotriene B4 (LTB4) and to leukotriene C4 (LTC4). LTC4, in turn, is converted to leukotrienes D4 (LTD4) and E4 (LTE4). LTC4, LTD4 and LTE4, also referred to as cysteinyl leukotrienes, interact with CysLT1 and CysLT2 receptors. As used herein, "leukotriene blocker" means a compound that: (1) inhibits a step in the leukotriene biosynthetic pathway; or (2) inhibits leukotriene receptor activation. Example of leukotriene blockers include: montelukast (SINGULAIR®; Merck; selective and orally active leukotriene receptor antagonist), zafirlukast (ACCOLATE®; AstraZeneca; selective peptide leukotriene receptor antagonist), zileuton (ZYFLO®; Abbott; orally active inhibitor of 5LO), prankulast, MK-571, MK-591, MK-886, BAYx1005, Cinalukast, Pobilukast edamine, MK-679 and ZD2138. In some embodiments of the invention, two or more leukotriene blockers are employed in combination. Preferred leukotriene blockers are montelukast (SINGULAIR®), a selective and orally active leukotriene receptor antagonist; zafirlukast (ACCOLATE®), a selective and competitive receptor antagonist of leukotriene $D_4$ (LTD$_4$) and leukotriene $E_4$ (LTD$_4$); and zileuton (ZYFLO®), an orally active inhibitor of 5LO.

Dosage and route of administration of the leukotriene blocker(s) will depend on the particular agent(s) employed. Safe and effective dosages and routes of administration for the various leukotriene blockers are known in the art. See, e.g., *Physician's Desk Reference* (PDR®) or vendor's package inserts. For example, the preferred dosage of zafirlukast (ACCOLATE®) in adult humans is 20 mg, twice daily, taken orally in tablet form. In another example, the preferred dosage of montelukast (SINGULAIR®) in adult humans is 10 mg, once daily, taken orally in tablet form.

Preferably, administration of the leukotriene blocker is commenced concurrently with the initiation of NO inhalation. Duration of leukotriene blocker administration will depend on the agent employed and the duration of the NO inhalation.

Pulmonary Injury

While the invention can be utilized advantageously during NO inhalation therapy in general, it is particularly useful for improving oxygenation in patients with acute pulmonary injury, including acute respiratory distress syndrome (ARDS). Examples of acute pulmonary injury include: diffuse pulmonary infection (e.g., viral, bacterial, fungal); aspiration (e.g., gastric contents, water in cases of near drowning, meconium in neonates); inhalation of toxins and irritants (e.g., chlorine gas, $NO_2$, smoke, ozone, high concentrations of oxygen); narcotic overdose pulmonary edema (e.g., heroin, methodone, morphine, dextropropoxyphene); non-narcotic drug effects (e.g., nitrofurantoin); immunologic response to host antigens (e.g., Goodpasture's syndrome, systemic lupus erythematosis); effects of nonthoracic trauma with hypotension ("lung shock") in association with systemic reaction to processes initiated outside the lung (e.g., gram-negative septicemia, hemorrhagic pancreatitis, amniotic fluid embolism, fat embolism); and post-traumatic lung injury including lung contusion, lung transplantation, cardiopulmonary bypass lung injury, and postpneumonectomy pulmonary edema.

Impaired HPV

The methods of the invention are useful for reducing, partially preventing or completely preventing NO inhalation-related impairment in HPV. Signs of an existing impairment in HPV include low blood oxygenation (hypoxemia), which can be indicated by blue color of patient, reduced levels of oxymetric saturation, change in mental status, neurologic dysfunction, dyspnea, tachycardia and hypotension. Symptoms of an existing impairment in HPV include shortness of breath and chest pain. Diagnosis of impairment or reduction in HPV is within ordinary skill in the art.

Patients at risk for development of impairment or reduction of HPV include patients with sepsis and patients with a potential lung inflammation. Lung inflammation can arise from conditions such as pneumonia or acute respiratory distress syndrome.

Impaired Responsiveness to NO Inhalation

The methods of the invention are useful for reducing, partially preventing or completely preventing loss of pulmonary vasodilatory responsiveness to NO inhalation. Loss of pulmonary vasodilatory responsiveness to NO means an inability of NO to increase oxygenation or to decrease pulmonary arterial pressure (PAP). Signs of inability to decrease PAP include reduced cardiac output and right heart failure, presenting as shock, edema and anasarca.

Patients at risk for loss of pulmonary vasodilatory responsiveness to NO inhalation include patients with sepsis and patients with a potential lung inflammation. Lung inflammation can arise from conditions such as pneumonia or acute respiratory distress syndrome.

Experimental Information

EXAMPLE 1

Anti-ROS Agents and Impairment of Pulmonary Vascular Responsiveness to NO

Figure 2B:
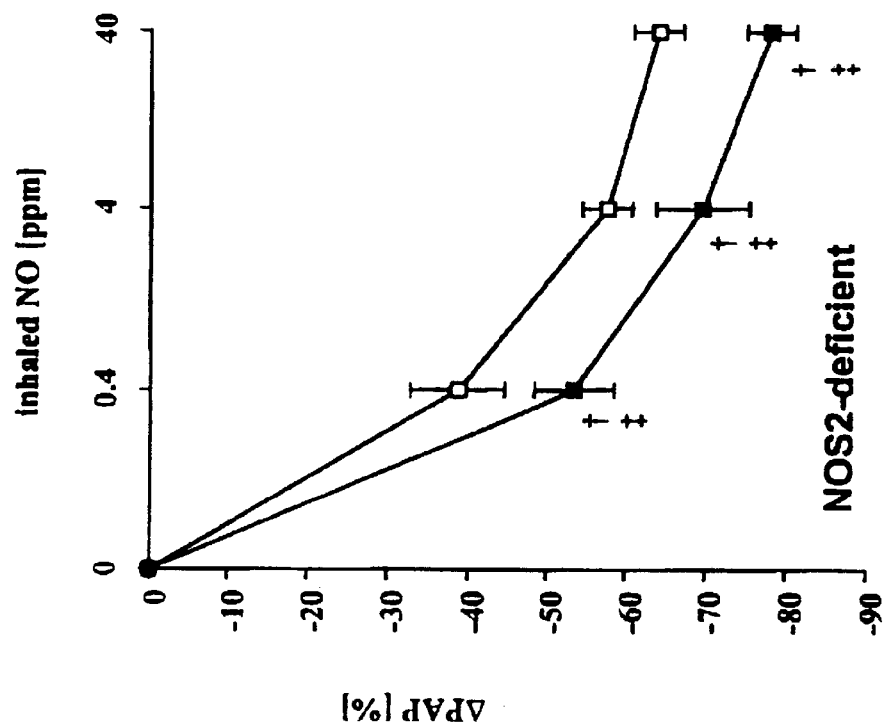
FIG. 2B is a dose-response curve for NO inhalation in lipopolysaccharide-pretreated (closed squared) and untreated (open squares) NOS2-deficient mice. Lipopolysaccharide-treated NOS2-deficient mice had a greater response to NO inhalation, as compared to untreated NOS2-deficient mice (†$P<0.05$) and lipopolysaccharide-pretreated wild-type mice (‡$P<0.001$). Data are expressed as mean±SE. $\Delta$PAP=change in pulmonary artery pressure as percent of its U46619-induced increase.
Figure 2A:
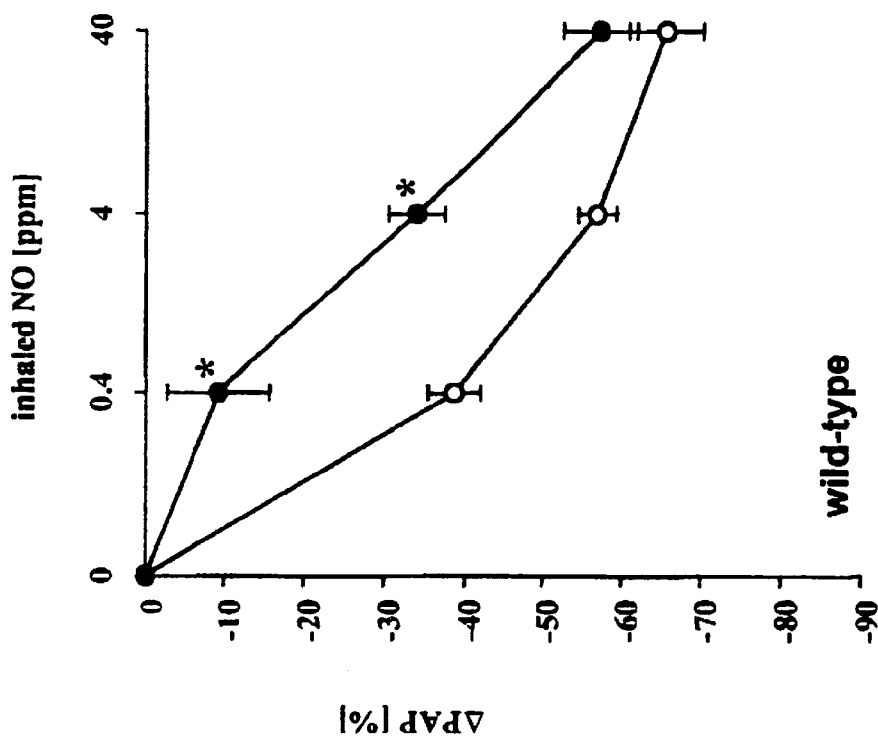
FIG. 2A is a dose-response curve for NO inhalation in lipopolysaccharide-pretreated (closed circles) and untreated (open circles) wild-type mice. The response to NO inhalation was impaired in lipopolysaccharide-pretreated wild-type mice, as compared to untreated wild-type mice (*$P<0.001$). Data are expressed as mean±SE. $\Delta$PAP=change in pulmonary artery pressure as percent of its U46619-induced increase.

Experimental evidence was obtained demonstrating that scavengers of reactive oxygen and reactive nitrogen species prevent the impairment of pulmonary vascular responsiveness to NO inhalation by endotoxin-challenged mice. These experiments were performed by using NOS2-deficient mice, in which prolonged NO inhalation together with an endotoxin-induced factor(s) other than NO impairs the ability of the pulmonary vasculature to vasodilate in response to subsequent NO inhalation. Responsiveness to NO inhalation was evaluated in isolated-perfused mouse lungs preconstricted with U46619. Wild-type mice treated with endotoxin 16 hours before isolation of lungs displayed impaired responsiveness to NO inhalation (FIG. 2A). NOS2-deficient mice treated with endotoxin displayed nonimpaired responsiveness to NO inhalation (FIG. 2B). Wild-type mice exposed to 20 ppm NO for 16 hours before isolation of lungs displayed nonimpaired responsiveness to NO inhalation. NOS2 deficient mice treated with endotoxin and exposed to 20 ppm NO for 16 hours displayed impaired responsiveness to NO inhalation (FIG. 3). NOS2-deficient control mice receiving saline instead of endotoxin and exposed to 20 ppm NO for 16 hours displayed nonimpaired responsiveness to NO inhalation. In wild-type mice treated with endotoxin, scavengers of reactive oxygen and nitrogen species, including N-acetyl cysteine (FIG. 5), dimethylurea, EUK8, and catalase prevented impairment of responsiveness to NO inhalation. N-acetyl-cysteine prevented the impairment of pulmonary vascular responsiveness to NO inhalation in endotoxin-challenged wild-type mice despite prolonged NO inhalation (FIG. 6).

Figure 5:
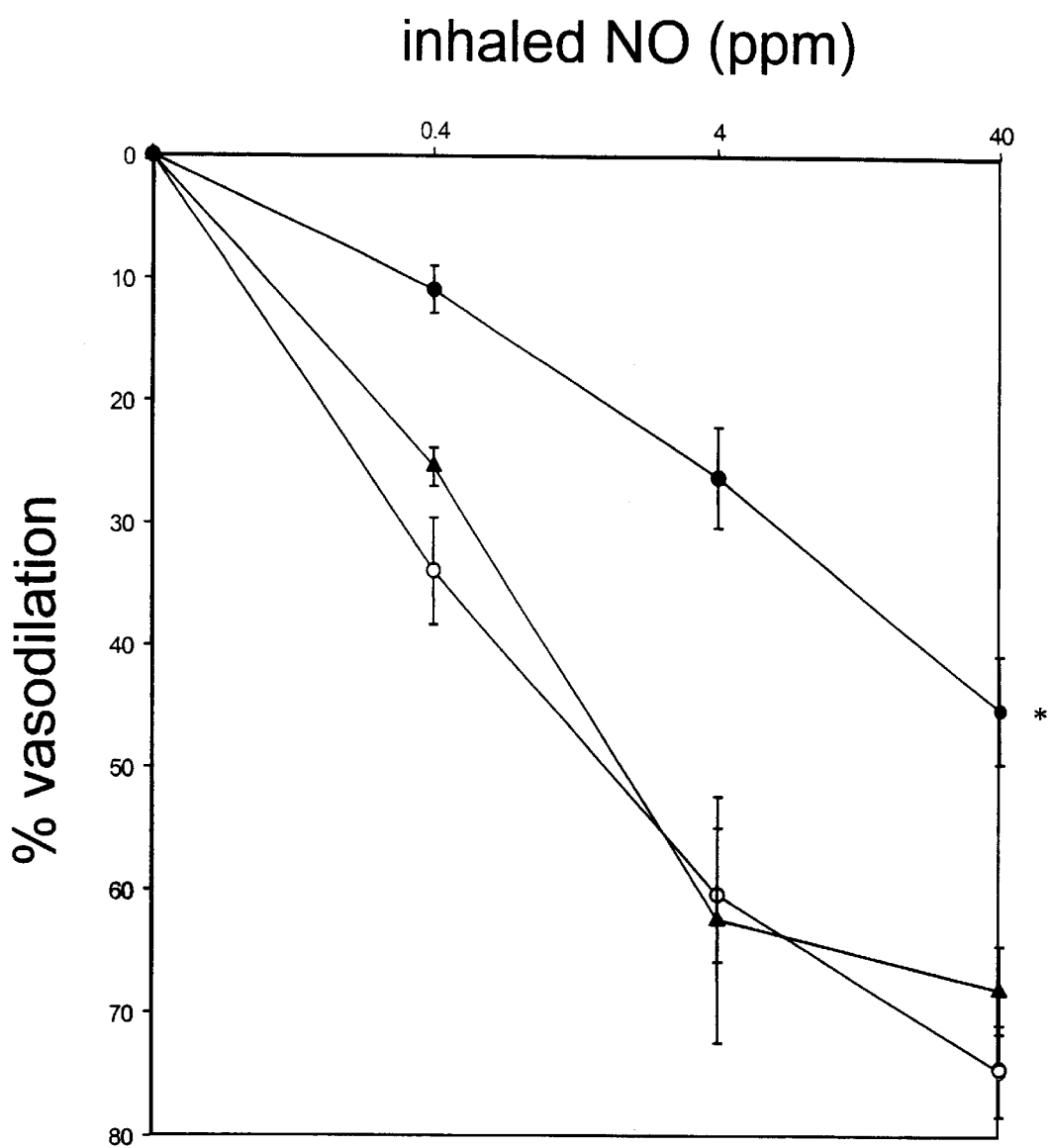
FIG. 5 is a graph summarizing data from experiments on the pulmonary vasodilator response to NO inhalation in lipopolysaccharide-challenged (closed circles) and control mice (open circles), and in lipopolysaccharide-challenged mice treated with N-acetylcysteine (150 mg/kg i.p.) simultaneously with lipopolysaccharide and repeated 3.5 hours later (closed triangles). The response to NO inhalation was attenuated in lipopolysaccharide-treated mice as compared to control mice (*$P<0.001$). Two doses of N-acetylcysteine (150 mg/kg) completely protected against polysaccharide-induced attenuation of vasoreactivity to NO inhalation. %vasodilation is change in pulmonary artery pressure as percent of U46619-induced increase. Data are expressed as mean±SE.
Figure 6:
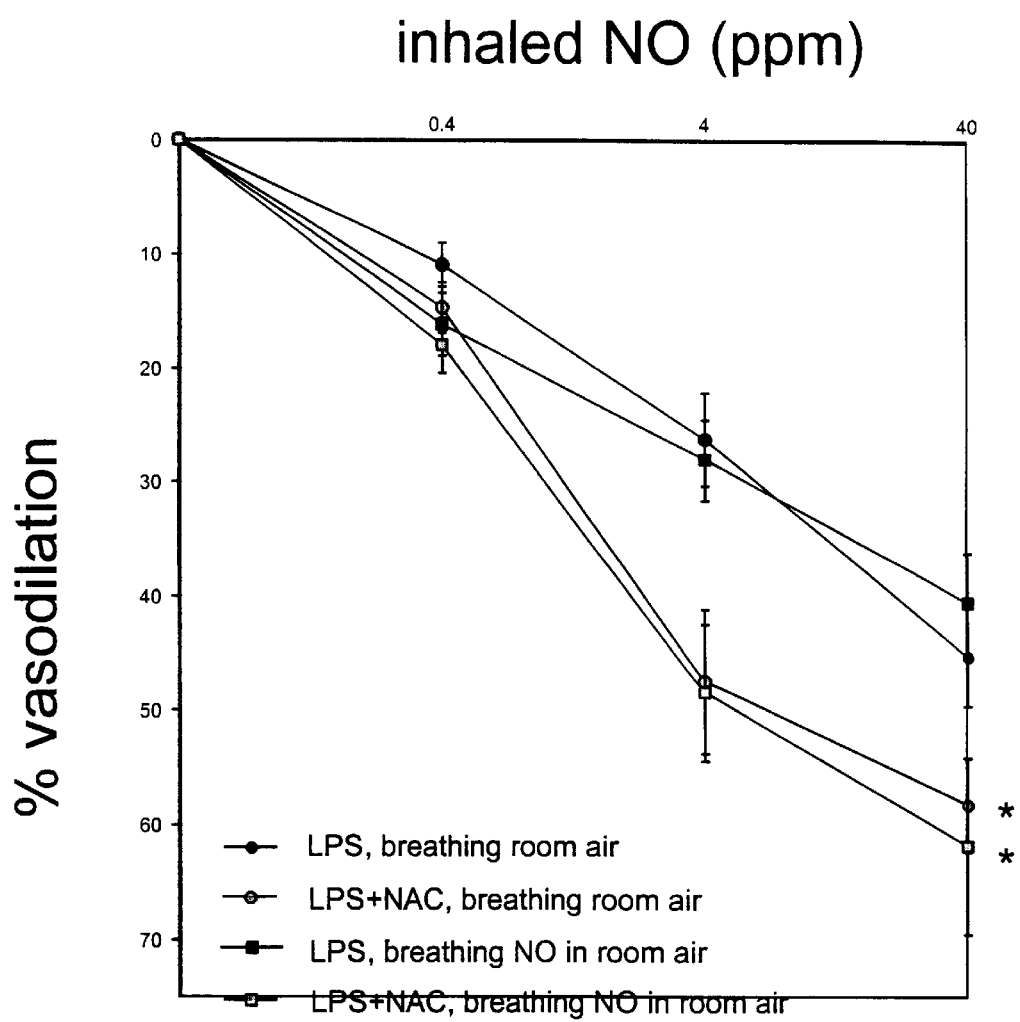
FIG. 6 is a graph summarizing data from experiments on the pulmonary vasodilator response to NO inhalation in lipopolysaccharide (LPS)-challenged mice that were treated with a simultaneous intraperitoneal injection of N-acetylcysteine or saline, and that breathed either room air or room air plus 20 ppm NO gas for 16 hours. The protective effect of N-acetyl-cycteine 150 mg/kg on the pulmonary vasodilator response to NO in lipopolysaccharide-challenged mice was preserved during prolonged NO inhalation. (*$P<0.05$ vs. LPS+saline in both groups).

The experimental results shown in FIG. 5 demonstrated that responsiveness to NO inhalation was preserved in endotoxin-challenged wild-type mice treated with N-acetylcysteine. The experimental results shown in FIG. 6 indicated that the mechanism responsible for the protective effect of N-acetylcysteine was not simply attributable to suppression of endotoxin-induced pulmonary NOS2 expression.

Methods and Materials

These investigations were approved by the Subcommittee for Research Animal Care of the Massachusetts General hospital. A total of 78 adult male mice weighing 20–35 g were studied, as listed in table 1 and outlined herein. NOS2-deficient mice (MacMicking et al., 1995, *Cell* 81:641–650) were provided by Dr. Carl Nathan. Mice of the same background (F1-generation of the parental strains SV129 and C57 Black/6) were used as wild-type mice (Hickey et al., 1997, *FASEB J.* 11:955–964).

Isolated, Perfused, and Ventilated Mouse Lung Model Mice were killed by intraperitoneal injection of pentobarbital sodium (200 mg/kg body weight) and placed in a 37° C. water-jacketed chamber (Isolated Perfused Lung Size 1 Type 839; Hugo-Sachs Elektronik, March-Hugstetten, Germany). The trachea was isolated and intubated, and the lungs were ventilated with 21% $O_2$, 6% $CO_2$ and 73% $N_2$ using a volume-controlled ventilator (model 687; Harvard Apparatus, South Natick, Mass.) at a ventilatory rate of 85 breaths/min and 2 cm $H_2O$ end-expiratory pressure. The tidal volume was adjusted to provide a peak inspiratory pressure of 10 cm $H_2O$ throughout each study. The lungs were exposed via a midline sternotomy, and a ligataure was placaed around the aorticopulmonary outflow tract. After injection of 10 IU heparin into the right ventricle, the pulmonary artery was cannulated with a stainless steel cannula (1 mm ID) via the right ventricle. The pulmonary venous effluent was drained via a stainless steel cannula (1 mm ID) placed through the apex of the left ventricle across the mitral valve and into the left atrium. Left atrial pressure was maintained at 2 mmHg. Lungs were perfused at a constant flow (50 ml. kg body weight$^{-1}$. min$^{-1}$; Ismatec Reglo-Analogue roller pump; Laboratoriumstechnik GmbH, Wertheim-Mondfeld, Germany) with a non-recirculating system at 37° C. The perfusate used was Hanks' Balanced Salt Solution (GibcoBRL, Grand Island, N.Y.) containing 1.26 mM $CaCl_2$, 5.33 mM KCl, 0.44 mM $KH_2PO_4$, 0.50 mM $MgCl_2$, 0.41 mM $MgSO_4$, 138.0 mM NaCl, 4.0 mM $NaHCO_3$, 0.3 mM $Na_2HPO_4$, and 5.6 mM glucose. Bovine serum albumin, 5%, and dextran, 5% (both from Sigma Chemical Co., St. Louis, Mo.), were added to the perfusate to prevent pulmonary edema, in the isolated, perfused, and ventilated rat lung, essentially as described in Holzmann et al., 1996, *Am. J. Physiol.* 271:L981–L986. Indomethacin, 30 mM (Sigma Chemical Co.), and 1 mM L-NAME (Sigma Chemical Co.) were added to the perfusate to inhibit endogenous prostaglandin and NO synthesis, respectively. Sodium bicarbonate was added to adjust the perfusate pH to 7.34–7.43.

Lungs were included in this study if they had a homogenous white appearance without signs of hemostasis or atelectasis and showed a stable perfusion pressure less than 10 mmHg during the second 5 min of an initial 10-min baseline perfusion period. Using these two criteria, approximately 15% of lung preparations from each group were discarded before study.

Pulmonary artery pressure (PAP) and left atrial pressure were measured via saline-filled membrane pressure transducers (Argon, Athens, Tex.) connected to a side port of the inflow and outflow cannulae, respectively. Airway pressure (Paw) was measured using a differential pressure transducer (model MP-45-32-871; Validyne Engineering Corp., Northridge, Calif.) connected to the inspiratory limb just before the Y piece. Pressure transducers were connected to a biomedical amplifier (Hewlett Packard 7754B, Andover, Mass.), and data were recorded at 150 Hz on a personal computer using an analog-to-digital interface with a data acquisition system (DI-220; Dataq Instruments, Akron, Ohio). The system was calibrated before each experiment.

For NO inhalation, NO gas (800 or 80 ppm NO in nitrogen, Airco, Murray Hill, N.J.) was blended (Oxygen Blender; Bird Corporation, Palm Springs, Calif.) with oxygen, carbon dioxide, and nitrogen to achieve a final concentration of 21% $O_2$, 6% $CO_2$, and the desired NO concentration. NO and higher oxidative states of NO ($NO_x$; CLD 700 AL; Eco Physics, Dürnten, Switzerland), oxygen (Hudson Ventronics Ddivision, Temecula, Calif.), and carbon dioxide (Datex CO2 monitor; Puritan-Bennett Corpration, Los Angeles, Calif.) concentrations were monitored continuously.

Pulmonary Vascular Response to NO inhalation after Lipopolysaccharide Challenge Wild-type mice and NOS2-deficient mice were injected intraperitoneally with 50 mg/kg body weight *Escherichia coli* 0111:B4 lipopolysaccharide (LPS; Difco Laboratories, Detroit, Mich.) dissolved in saline 16 h before isolated lung perfusion. This time point was chosen based on previous studies in rats (Holzmann et al., 1996, *Am. J. Physiol.* 271:L981–L986). Untreated wild-type and NOS2-deficient mice served as controls.

After an initial 10-min baseline perfusion period, pulmonary vasoconstrictin was induced by continuous infusion of the thromboxane $A_2$ analog U-46619 (Cayman Chemicals, Ann Arbor, Mich.). The infusion rate was adjusted to provide a stable increase in PAP of 5 or 6 mmHg. Then, a dose-response curve to inhaled NO was obtained by sequentially ventilating the lungs with 0.4, 4, and 40 ppm NO for 5 min each. After each period of NO ventilation, the PAP was allowed to return to the pre-NO elevated baseline. U-46619 infusion was readjusted if the PAP was not within a range of ±10% of the pre-NO value at 5 min after discontinuation of NO inhalation. The vasodilator response to inhaled NO (APAP) was measured as the change in PAP produced by inhaled NO (PAP after 5 min of NO inhalation minus PAP pre-NO) as a percentage of the increase in PAP induced by U-46619 (PAP pre-NO minus PAP at initial baseline).

Effect of NO Exposure on Pulmonary Vascular Response to Inhaled NO Four groups of mice breathed 20 ppm NO for 16 h. One group of wild-type mice and one group of NOS2-deficient mice were injected with 50 mg/kg lipopolysaccharide intraperitoneally immediately before NO exposure. Additional wild-type and NOS2-deficient mice groups were exposed to NO inhalation without receiving lipopolysaccharide. After 16 h of NO exposure, the lungs were isolated and perfused as described previously. Pulmonary vasoconstriction was induced by infusion of U46619, and the vasodilator response to 0.4, 4, and 40 ppm NO was measured.

During ambient-pressure NO exposure, animals were maintained in 40-1 acrylic chambers. NO and $NO_x$ concentrations were controlled carefully using soda lime[22] at a high fresh gas flow rate of NO (10,000 ppm NO in nitrogen; Airco, Murry Hill, N.J.), air, and oxygen, as previously described (Steudel et al., 1998, 101:2468–2477).

Two additional groups of NOS2-deficient mice were treated with lipopolysaccharide (50 mg/kg intraperitoneal) and then exposed to 0.2 and 2 ppm NO inhalation, respectively. Sixteen hours later, isolated lung perfusion studies measuring the degree of pulmonary vasodilation produced by 0.4, 4, and 40 ppm inhaled NO were performed.

Wet-to-Dry Lung Weight Ratio At the end of each experiment, both lungs, excluding hilar structures, were excised and weighed (wet weight). Thereafter, the lungs were dried in a microwave oven for 60 min, as previously described (Holzmann et al., supra), and then reweighed (dry weight). Wet-to-dry lung weight ratios were calculated by dividing the wet weight by the dry weight.

Statistical Analysis All data are expressed as the mean±standard error (SE). To compare groups, a two-way analysis of variance was performed. When significant differences were detected by analysis of variance, a post hoc least significant difference test for planned comparisons was used (Statistica for Windows; StatSoft, Inc., Tulsa, Okla.). Statistical significance was assumed at a P value<0.05.

Results

Infusion of U46619 caused a stable increase of the PAP at a constant perfusate flow, which was reversible after discontinuing U46619 at the end of the experiment. The dose of U46619 necessary to increase the PAP by 5 or 6 mmHg did not differ in lipopolysaccharide-pretreated and untreated wild-type and NOS2-deficient mice.

Mice injected with intraperitoneal lipopolysaccharide had piloerection, diarrhea, and lethargy to a similar degree in both wild-type and NOS2-deficient mice. The mortality rate 16 h after lipopolysaccharide injection was approximately 15% and did not differ between the two mouse strains.

Pulmonary Vascular Response to NO Inhalation Inhalation of NO decreased the PAP in a dose-dependent manner in all groups. FIG. 1 is a tracing from a representative experiment measuring pulmonary artery pressure (PAP; equivalent to perfusion pressure) and left atrial pressure (LAP) in an isolated-perfused lung of an untreated wild-type mouse. The stable thromboxane $A_2$ analog U46619 was infused to increase PAP by 5 or 6 mmHg. Lungs were ventilated with varying concentrations of NO gas (0.4, 4.0, and 40 ppm) for 5 minutes each. After ventilation with NO was discontinued, PAP was allowed to return to the pre-NO level. These results demonstrate that, in isolated-perfused lungs of a mouse, it is feasible to measure pulmonary artery pressure, to induce stable pulmonary vasoconstriction, and to reduce pulmonary vasoconstriction by ventilation with low concentrations of NO gas.

In the isolated-perfused lungs of wild-type mice that underwent lipopolysaccharide challenge, PAP decreased 79% and 45% less in response to 0.4 and 4 ppm inhaled NO, respectively, compared with untreated animals (P<0.001; FIG. 2A). The pulmonary vasodilator response to 40 ppm NO did not differ between these groups. Response to inhaled NO in untreated NOS2-deficient mice did not differ from that of untreated wild-type mice. In contrast, lungs obtained from lipopolysaccharide-challenged NOS2-deficient mice showed greater vasodilatation to inhaled NO than the lungs of lipopolysaccharide-treated wild-type mice (P<0.001 at each NO dose; FIG. 2B). Moreover, NO-induced vasodilation was enhanced in lipopolysaccharide-treated NOS2-deficient mice, compared with untreated NOS-2deficient or wild-type mice (P<0.05, respectively, at each NO dose; FIG. 2B).

Data presented in FIG. 2A shows that endotoxin-challenge impaired the ability of wild-type mice to dilate their pulmonary vasculature in response to ventilation with 0.4 and 40 ppm NO (*P<0.001). Data presented in FIG. 2B shows that endotoxin-challenge did not impair the pulmonary vasodilator response to inhaled NO. Rather, endotoxin augmented the ability of the pulmonary vasculature of NOS2-deficient mice to dilate in response to ventilation with 0.4, 4, and 40 ppm NO (†P<0.05). The pulmonary vasodilator response to inhaled NO was greater in endotoxin-challenged NOS2-deficient mice than in endotoxin-challenged wild-type mice (‡P<0.001).

Pulmonary Vascular Response to NO After NO Inhalation Exposure To investigate the role of molecular NO in the development of hyporesponsiveness to NO inhalation, we studied lipopolysaccharide-treated and untreated NOS2-deficient and wild-type mice that breathed air supplemented with 20 ppm NO for 16 h. Previous NO inhalation exposure did not alter the responsiveness to subsequently inhaled NO in perfused lungs obtained from untreated wild-type or NOS2-deficient mice or in lipopolysaccharide-pretreated wild-type mice. In contrast, the pulmonary vasodilator response to NO inhalation was decreased in lipopolysaccharide-pretreated NOS2-deficient mice exposed to ambient NO for 16 h, compared with non-NO-exposed lipopolysaccharide-pretreated NOS2-deficient mice. In isolated-perfused lungs from NOS2-deficient mice exposed to 20 mm ambient NO for 16 h, the subsequent vasodilator responsiveness to NO inhalation was impaired after pretreatment with lipopolysaccharide (vs. untreated controls) at 0.4

(ΔPAP−24±4% vs. −42±4%; P<0.05) and 4 ppm NO (ΔPAP−39±5% vs. −58±4%; P<0.01), but not at 40 ppm NO (ΔPAP−55±3% vs. −62±5%; P=not significant; FIG. 3. Similar to animals without previous NO inhalation exposure, NO-induced vasodilation was reduced in lipopolysaccharide-pretreated wild-type mice, compared to untreated wild-type mice that had breathed 20 mm NO for 16 h before lung perfusion experiments (FIG. 3).

After prolonged NO exposure, endotoxin-challenged NOS2-deficient mice were less responsive to short-term NO inhalation than were NOS2-deficient mice that did not receive lipopolysaccharide (*P<0.05). Similarly, after prolonged NO exposure, lipopolysaccharide-pretreated wild-type mice were less responsive to short-term NO inhalation than were wild-type mice that did not receive lipopolysaccharide (*P<0.05). These observations demonstrate that prolonged breathing of 20 mm NO does not impair the pulmonary vasodilator response to subsequent ventilation with NO in untreated wild-type or NOS2-deficient mice. In contrast, prolonged breathing of 20 mm NO markedly impaired the pulmonary vasodilator response to subsequent ventilation with NO in endotoxin-challenged NOS2-deficient mice (compare with data presented in FIG. 2B).

Figure 4:
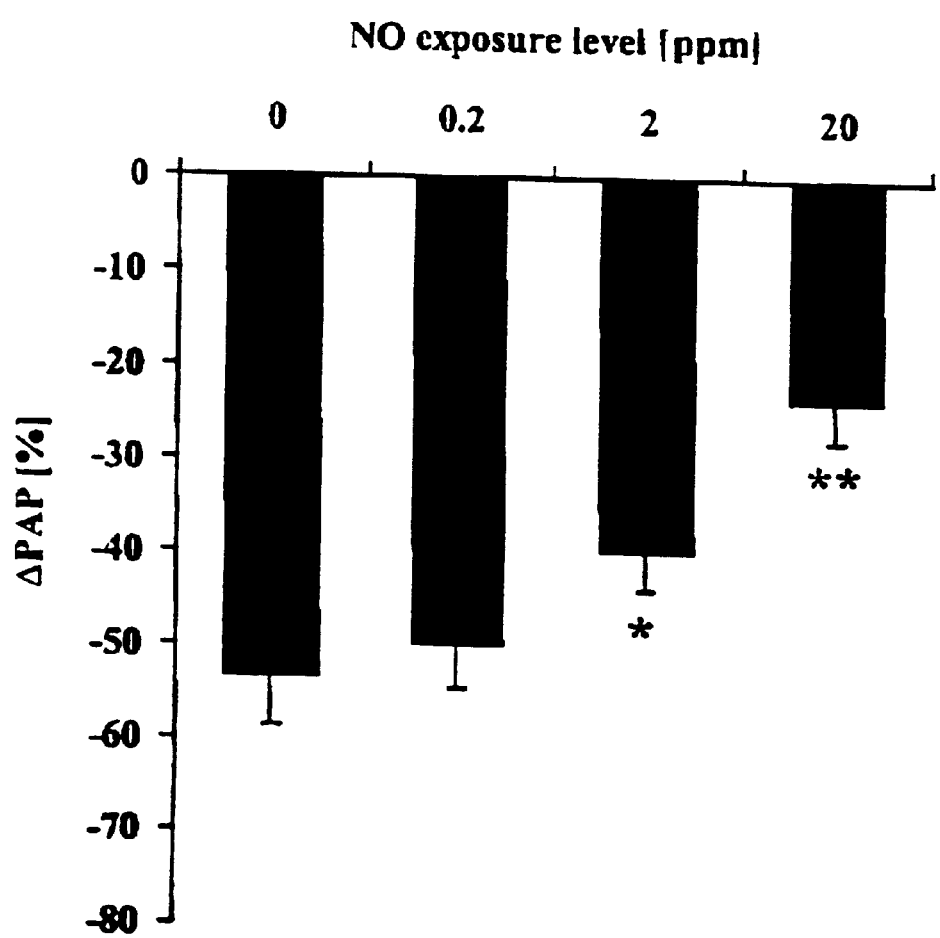
FIG. 4 is a histogram summarizing data from experiments on the effects of breathing 0, 0.2, 2.0 and 20 ppm NO for 16 hours after lipopolysaccharide challenge on the subsequent vasodilation in response to short-term inhalation of 0.4 ppm NO gas, in isolated-perfused lungs obtained from NOS2-deficient mice. Exposure to 2 and 20 ppm NO gas decreased the pulmonary vasodilatory response to NO. Data are expressed as mean±SE. *$P<0.05$; **$P<0.001$ versus 0 ppm NO exposure for 16 hours.

To determine whether the inhalation of a lower level of NO for 16 h would impair vasoreactivity to short-term NO inhalation during lung perfusion, lipopolysaccharide-treated NOS2-deficient mice were exposed to 0.2 and 2 ppm NO inhalation. Breathing 0.2 ppm NO for 16 h after lipopolysaccharide administration did not cause subsequent hyporesponsiveness to short-term inhaled NO in NOS2-deficient mice. However, breathing 2 ppm NO for 16 h decreased the vasodilator response to 0.4 ppm NO inhalation, compared with the response in control mice (P<0.05; FIG. 4).

Wet-to-Dry Lung Weight Ratios The absence of pulmonary edema was confirmed by unchanged wet-to-dry lung weight ratios after perfusion. There was no difference between lipopolysaccharide-pretreated wild-type (wet weight–dry weight: 4.3±0.2) and NOS2-deficient (4.8±0.1) mice, or untreated wild-type (4.6±0.1) and untreated NOS2-deficient (4.6±0.1) mice. Exposure to NO inhalation for 16 h did not alter the wet-to-dry lung weight ratios in lipopolysaccharide-pretreated wild-type (4.9±0.1) and NOS2-deficient (5.1±0.2) mice or in untreated wild-type (4.5±0.3) and untreated NOS2-deficient (4.8±0.1) mice, compared with unexposed mice. Wet-to-dry lung weight ratios did not correlate with the vasodilator response to inhaled NO.

Effect of N-Acetylcysteine We investigated whether scavenging of reactive oxygen species with N-acetylcysteine (NAC) prevented the impairment of the pulmonary vasodilatory response to NO inhalation in endotoxin-challenged mice. Wild-type mice were treated with endotoxin (E. coli 011:B4-LPS, 50 mg/kg i.p.) followed by administration of normal saline or NAC (150 mg/kg i.p.) immediately, and 3.5 hours later (n=5). Additional endotoxin-challenged mice treated with NAC breathed 20 mm NO for 16 hours.

Mouse lungs were isolated, perfused, and ventilated 16 hours after endotoxin challenge. Lungs from mice treated with saline alone and breathing room air served as controls (n=10). Pulmonary vasoconstriction was induced with U46619, and the vasodilator response to 0.4, 4.0 and 40 ppm NO by inhalation was measured. Vasodilation in response to 0.4, 4.0 and 40 ppm NO in endotoxin-challenged mice was 32±13%, 43±10%, and 53±8%, respectively, compared to that in control mice (p<0.001 vs. control) (FIG.6). In contrast, the vasodilator response to NO inhalation in endotoxin-challenged mice treated with NAC did not differ from that in control mice (75±14%, 103±15%, and 91±7%, respectively (p<0.001 vs. LPS) (FIG. 6). Responsiveness to NO inhalation was also preserved in endotoxin-challenged, NAC-treated mice exposed to 20 mm NO. This indicated that NAC did not preserve responsiveness to acute NO inhalation by preventing the endotoxin-induced increase in pulmonary NO levels. These results demonstrated the effectiveness of NAC (a scavenger of reactive oxygen species) in preventing endotoxin-induced impairment of responsiveness to NO inhalation.

EXAMPLE 2

HPV and Scavengers of Reactive Oxygen Species

Experimental evidence was obtained demonstrating that scavengers of reactive oxygen species prevent the impairment of HPV in endotoxin-challenged mice. To investigate the role for NOS2 in endotoxin-induced impairment of HPV, we compared ability of to redistribute pulmonary blood flow after left mainstream bronchus occlusion (LMBO) in wild-type mice and in mice with a congenital deficiency of NOS2. For these experiments, we developed a murine LMBO model. This allowed us to evaluate the impact of endotoxin on HPV in intact mice.

Figure 7:
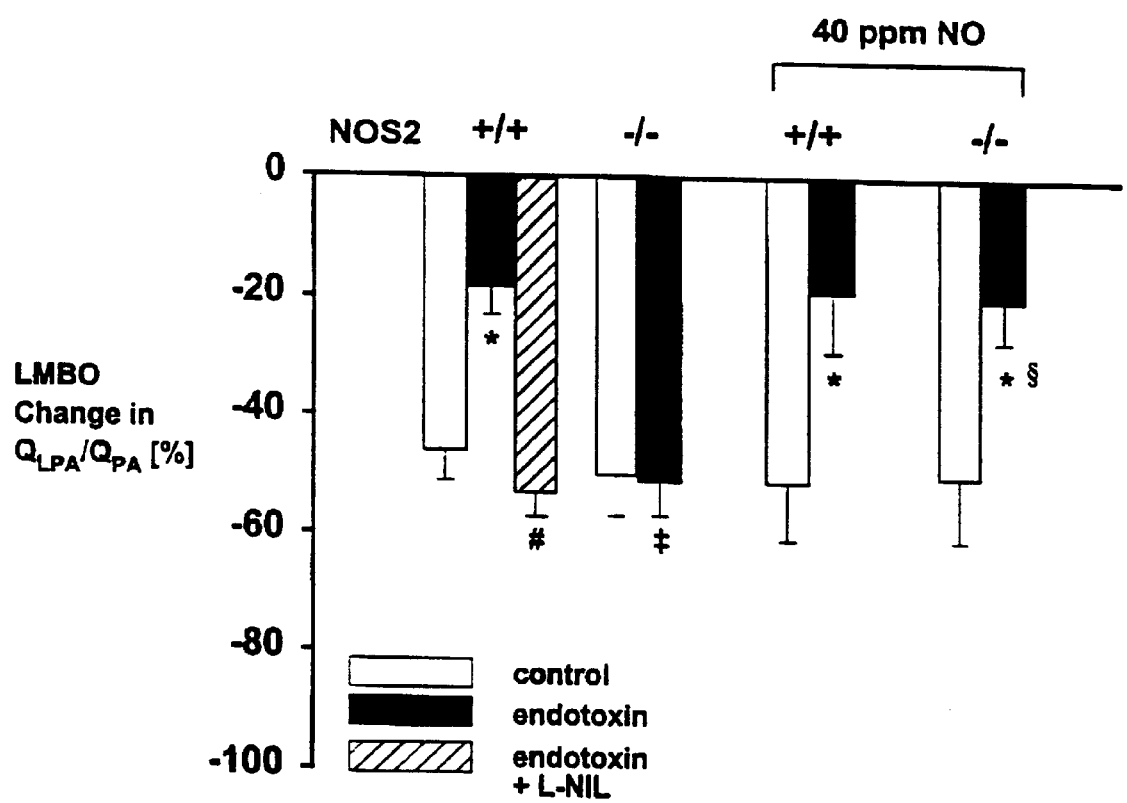
FIG. 7 is a histogram summarizing data from experiments on change in fractional blood flow to the left lung (QLPA/QPA) 5 minutes after left mainstem bronchus occlusion (LMBO) in wild-type mice (+/+) and NOS2-deficient mice (-/-) treated with saline (control, open bars; n=7), endotoxin (endotoxin, closed bars; n=6), or endotoxin with 5 mg/kg L-NIL intraperitoneally (endotoxin with L-NIL (a selective NOS2 inhibitor), striped bar; n=5) administered 3 hours after the endotoxin challenge. (*$P<0.05$, endotoxin versus control; $P<0.01$, wild-type versus NOS2-deficient; #$P<0.01$ endotoxin+L-NIL versus endotoxin alone). Measurements were obtained following 1 hour after discontinuation of breathing air or 40 ppm NO in air for 22 h (§$P<0.05$ NO versus without NO). Endotoxin challenge caused a marked reduction of pulmonary blood flow redistribution after LMBO in wild-type, but not in NOS2-deficient mice. After prolonged inhalation of 40 ppm NO, endotoxin-treated NOS2-deficient mice, measured 1 hour after discontinuation of NO inhalation, showed the same loss of HPV as endotoxin-treated wild-type mice. Saline-treated NOS2-deficient mice and wild-type mice breathing 40 ppm NO for 22 hours retained their ability to redistribute pulmonary blood flow after LMBO, when measured 1 hour after discontinuing NO inhalation.

The results shown in FIG. 7 demonstrated that LMBO caused a redistribution of pulmonary blood flow away from the hypoxic left lung as reflected in a negative change in the ratio of left lung blood flow to total lung blood flow ($Q_{LPA}/Q_{PA}$ ratio). Endotoxin challenge caused a marked reduction of pulmonary blood flow redistribution after LMBO in wild-type mice (*P<0.05, endotoxin versus control) but not in NOS2-deficient mice (P<0.01, versus wild-type mice). Early administration of L-NIL prevented the reduction in LMBO-induced pulmonary blood flow redistribution (#P<0.01 versus endotoxin-challenged mice not treated with L-NIL). After prolonged inhalation of 40 ppm NO, endotoxin-treated NOS2-deficient mice showed the same loss of HPV as did endotoxin-challenged wild-type mice (§P<0.05 NO versus without NO). Saline-challenged NOS2-deficient mice and wildtype mice breathing 40 ppm NO for 22 hours retained their ability to redistribute pulmonary blood flow after LMBO, when measured 1 hour after discontinuing NO inhalation. These results show that increased pulmonary NO levels due to endotoxin-induced NOS2 expression or due to NO inhalation are required to impair HPV after challenge with endotoxin. However, prolonged exposure to increased pulmonary NO levels alone are insufficient to impair HPV (as measured 1 hour after discontinuation of NO inhalation).

Figure 8:
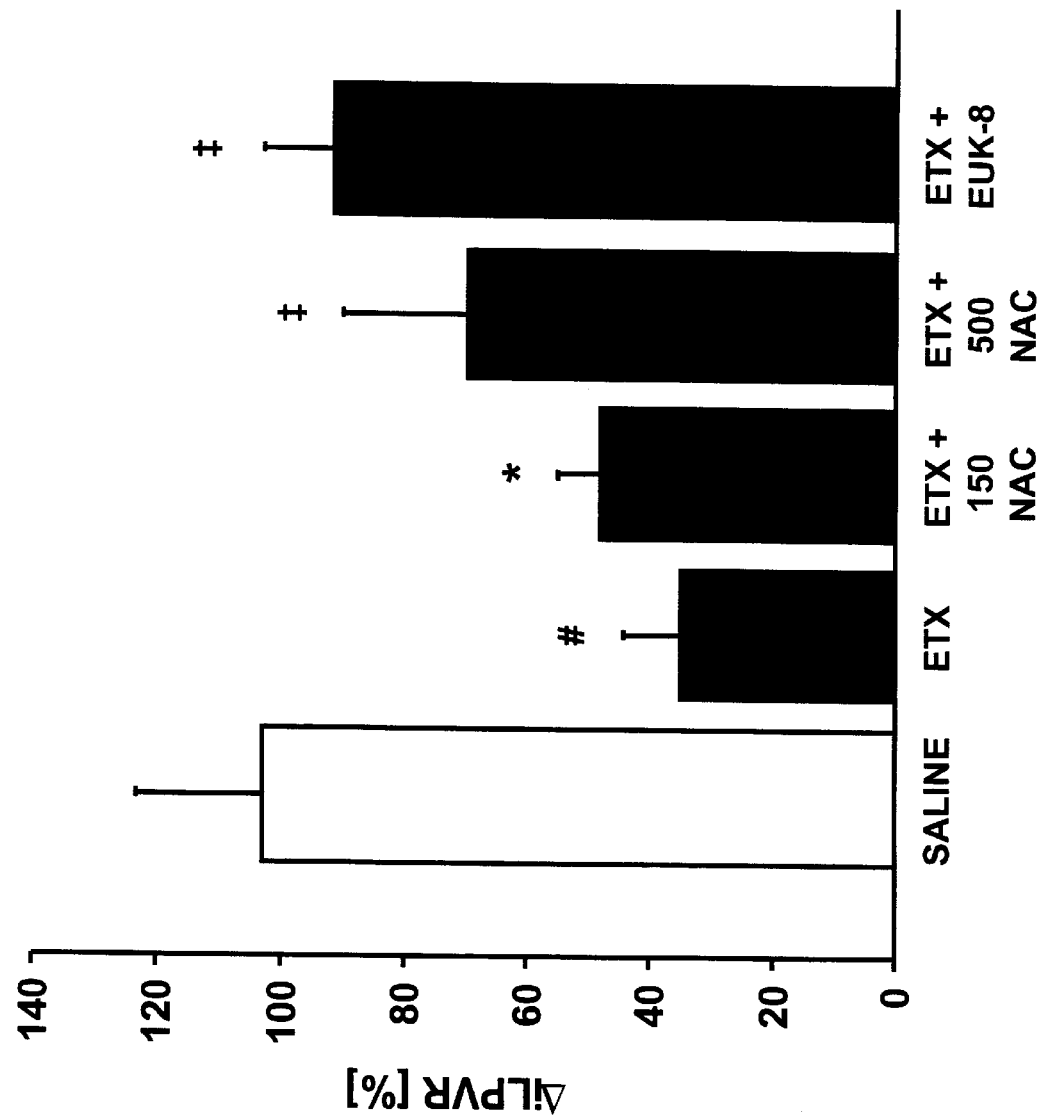
FIG. 8 is a histogram summarizing results from experiments measuring the change in incremental left pulmonary vascular resistance, $\Delta$iLPV, in response to LMBO—a measure of hypoxic pulmonary vasoconstriction (HPV). HPV was impaired in wild-type mice challenged with endotoxin (ETX; #$P<0.05$ versus saline-challenged mice). HPV was preserved in endotoxin-challenged mice treated with 500 mg/kg (‡<0.05 versus untreated endotoxin-challenged mice), but not 150 mg/kg (*$P<0.05$ versus saline-challenged mice), N-acetylcysteine (NAC; intraperitoneal administration of simultaneously with endotoxin). HPV was completely preserved in endotoxin-challenged mice treated with EUK-8, a scavenger of superoxide, hydrogen peroxide and peroxynitrite (‡$P<0.05$ versus untreated endotoxin-challenged mice).

We performed experiments on the change in incremental left pulmonary vascular resistance, ΔiLPV, in response to LMBO—a measure of HPV. HPV was impaired in wild-type mice challenged with endotoxin (FIG. 8). HPV was preserved in endotoxin-challenged mice treated with N-acetylcysteine at 500 mg/kg, but not 150 mg/kg (intraperitoneal administration simultaneously with endotoxin). HPV was completely preserved in endotoxin-challenged mice treated with EUK-8, a scavenger of both superoxide, hydrogen peroxide, and peroxynitrite.

From the above experiments we found that NOS2 deficiency protected mice from endotoxin-induced impairment of HPV. We further found that scavengers of reactive oxygen species prevented impairment of HPV in endotoxin-challenged, wild-type mice (FIG. 8).

Six lines of evidence supported these conclusions: (1) in wild-type mice LMBO increased pulmonary vascular resistance (PVR) in the left lung, but 22 hours after endotoxin challenge LMBO-induced left lung vasoconstriction was impaired; (2) in endotoxin-challenged NOS2-deficient mice not exposed to NO, LMBO-induced left lung vasoconstriction was unimpaired (FIG. 7); (3) in endotoxin-challenged NOS2-deficient mice exposed to 40 ppm NO for 22 hours, LMBO-induced left lung vasoconstriction was impaired (FIG. 7); (4) prolonged NO inhalation alone did not impair HPV in mice, (FIG.); (5) N-acetylcysteine or EUK-8 prevented impairment of HPV in endotoxin-challenged wild-type mice (FIG. 8); and (6) HPV was not impaired in endotoxin-challenged wild-type mice treated with N-acetylcysteine and exposed to 20 ppm NO for 22 hours.

Methods and Materials

After institutional approval by the Massachusetts General Hospital Subcommittee on Research Animal Care, we studied SV129/B6F1 wild-type mice (F1-generation progeny of SV129 and C57 BL/6 mice) and SV129 wild-type mice (The Jackson Laboratory, Bar Harbor, Me., USA), as well as NOS2-deficient mice with a SV129 and C57BL/6 hybrid background (MacMicking et al., 1995, Cell 81:641–650) (provided by C. Nathan, Cornell University, New York, N.Y.). In supplemental studies, NOS2-deficient mice (18), backcrossed 10 generations onto a C57BL/6 background (C57BL/6-Nos2tmlLau, N10-backcross generation; The Jackson Laboratory), and wild-type C57BL/6 were studied.

Experimental groups matched for animal age, body weight, and sex were used. Male and female mice with an age range of 2–5 months,weighing 18–30 g, were studied.

Group 1: controls. SV129/B6F1 wild-type mice (n=5), SV129 wild-type mice (n=7), and NOS2-deficient mice (n=7) received an intraperitoneal injection of 0.2 mL saline and were studied 22 hours later.

Group 2: endotoxin-treated. SV129/B6F1 wild-type mice (n =5), SV129 wild-type mice (n=6), and NOS2-deficient mice (n=6)were studied 22 hours after a challenge with an intraperitoneal injection of 10 mg/kg *Escherichia coli* O11 B4 endotoxin dissolved in 0.2 mL saline. Additionally, C57BL/6 wild-type mice (n=7) and C57BL/6-Nos2tmlLau mice (n=5) were studied 22 hours after a challenge with an intraperitoneal injection of 10 mg/kg endotoxin dissolved in 0.2 mL saline.

Group 3: endotoxin-treated+L-NIL. SV129/B6F1 wild-type mice (n=5) were injected intraperitoneally with 10 mg/kg *E. coli* O11 B4 endotoxin dissolved in 0.2 mL saline. Three hours after the endotoxin challenge, mice were treated with L-NIL 5 mg/kg intraperitoneally. Studies were performed 22 hours after the endotoxin challenge. In additional SV129/B6F1 mice with (n=5) and without (n=4) a prior challenge of endotoxin (22 hours earlier), the acute response to an intravenous bolus of 5 mg/kg L-NIL administered during LMBO, was studied. We chose a dose of 5 mg/kg intraperitoneal L-NIL because similar doses have been shown to effectively inhibit NOS2 activity in vivo in rodent models of inflammation (Schwartz et al., 1997, *J. Clin. Invest.* 100:439–448).

Group 4: prolonged exposure to 4 or 40 ppm NO. Saline-treated SV129 wild-type mice (n=5) and NOS2-deficient mice (n=5) breathed 40 ppm NO in air for 22 hours and were studied 1 hour after discontinuation of NO inhalation. SV129 wild-type mice (n=5) and NOS2-deficient mice (n=5) breathed 40 ppm NO in air for 22 hours after challenge with 10 mg/kg endotoxin intraperitoneally and were studied 1 hour after discontinuation of NO inhalation. Additional NOS2-deficient mice (n=4) breathed 4 ppm of NO in air for 22 hours after challenge with 10 mg/kg endotoxin intraperitoneally and were studied 1 hour after discontinuation of NO inhalation.

Group 5: continuous $PaO_2$ and $PvO_2$ measurements. $PaO_2$ was assessed continuously before and during LMBO in SV129/B6F1 wild-type mice (n =3) and NOS2-deficient mice (n=3) 22 hours after challenge with 10 mg/kg endotoxin intraperitoneally. $PvO_2$ was assessed continuously before and during LMBO in SV129/B6F1 wild-type mice (n=4) and NOS2-deficient mice (n=4) 22 hours after challenge with 10 mg/kg endotoxin intraperitoneally. In saline-treated SV129 wild-type mice, $PaO_2$ (n=4) and $PvO_2$ (n=4) were studied before and during LMBO under control conditions, without a prior challenge of endotoxin.

Group 6: pulmonary vascular response to increasing doses of intravenous angiotensin II. SV129/B6F1 wild-type mice treated with endotoxin (n=5) or with saline (n=3) were studied 22 hours after the challenge.

Experimental preparation. Mice were anesthetized by intraperitoneal injection of ketamine (0.1 mg/g body weight [bw]). Tracheostomy and arterial catheterization were performed as described previously (Steudel et al., 1997, *Circ. Res.* 81:34–41). A custom-made endotracheal tube (22G Angiocath; Becton Dickinson Healthcare Systems, Sandy, Utah, USA), combined with a 2 French Fogarty arterial embolization catheter (Baxter Healthcare Corp., Irvine, Calif., USA) was inserted into the trachea, with the balloon tip of the Fogarty catheter initially remaining in the trachea. Volume-controlled ventilation was initiated at a respiratory rate of 110–120 breaths per minute, at $FiO_2$ 1.0, a peak inspiratory pressure of 13 cm H2O, and a positive end-expiratory pressure level of 2–3 cm H2O. A right parasternal thoracotomy was performed, and a small-vessel ultrasonic flow probe (1RB; Transonic Instruments, Ithaca, N.Y.) was placed around the right pulmonary artery and fixed in position using a micromanipulator (X-tra Hand; TechniTool, Plymouth, Pa.). A 4–0 silk suture was positioned around the left main pulmonary artery to allow transient vascular occlusion. A pulmonary artery catheter (PE10) was inserted into the main pulmonary artery by direct puncture. In other experiments, a lower thoracic aortic flow probe was placed as reported previously (Steudel et al., supra).

In some studies, the pulmonary vein draining the right middle lobe was punctured with a 30 G needle, connected to PE10 tubing, and secured with a microclip to assess left atrial pressure (PLA). To measure the partial pressure of oxygen in the aorta ($PaO_2$), a flexible polarographic Clark-type $PO_2$ electrode (LICOX A3-Revoxode, 1.5 Fr.; GMS-Gesellschaft fuer medizinische Sondentechnik, Kiel, Germany), was advanced into the aortic arch -via the carotid artery. To measure the partial pressure of oxygen in the pulmonary artery ($PvO_2$), the right ventricular outflow tract was punctured, and the oxygen electrode was advanced into the pulmonary artery. Electrodes were calibrated before and after each experiment in air at ambient pressure using a test probe barrel. Anesthesia was maintained with intraperitoneal ketamine (0.1 mg/g bw) and xylazine (0.01 mg/g bw) injections with intraperitoneal pancuronium (0.002 mg/g bw) added to produce muscle relaxation.

Bloodflow and pressure measurements. Mean systemic arterial pressure (PSA), mean pulmonary artery pressure (PPA), and in some studies PLA, were continuously monitored using biomedical amplifiers (Hewlett Packard 8805C, Palo Alto, Calif.; Siemens Sirecust 960, Danvers, Mass.). Mean lower thoracic aortic flow (QLTAF) and right pulmonary artery flow (QRPA) were measured with small vessel flow probes connected to a flowmeter (T106; Transonic Instruments). In some experiments, left ventricular end-diastolic pressure was measured with a 1.4 Fr. Millar catheter. The catheter was advanced through the right carotid artery into the left ventricle. All measured signals were transferred to an analog-to-digital converter, displayed on a computer screen, and recorded at 640 Hz using a data acquisition system (DI 220; Dataq Instruments, Akron,Ohio) on a personal computer. All monitoring equipment was calibrated before each experiment.

Differential measurement of left and right pulmonary artery flow. To assess the contribution of QRPA and left pulmonary artery flow (QLPA) to total pulmonary artery flow (QPA), transient occlusion (90 seconds) of the left pulmonary artery (QLPA) was performed. QRPA during acute left pulmonary artery occlusion was considered to be QPA (i.e., cardiac output) and correlated closely (r2=0.88; y=0.95x+0.38; n=9) with QLTAF. QLPA was calculated as the difference between QRPA during left pulmonary artery occlusion (QPA) and QRPA with a patent left pulmonary artery (QLPA=QPA−QRPA). Absolute values of respective flows were recorded, and the fractional distribution of flow to the right and left lungs (QRPA/QPA and QLPA/QPA) was calculated.

QPA was assessed by measurement of QRPA during transient occlusion of the left pulmonary artery (QLPA) because blood flow is lost to the upper extremities and the head when measured at the lower thoracic aorta. Moreover, adding a second flow probe increases the likelihood of error, because of the small size of the mouse, and increases surgical trauma and stress to the animal.

Unilateral alveolar hypoxia. To induce regional (i.e., left lung) alveolar hypoxia, the left mainstem bronchus was reversibly occluded (LMBO) by advancing a Fogarty catheter into the left mainstem bronchus and inflating the balloon tip under visual control. Complete collapse of the left lung was visually observed within about a minute and confirmed by transient overinflation of the right lung. PPA, PSA, and QRPA were continuously measured during LMBO. In some experiments, the collapsed left lung was reinflated with 5% $CO_2$ in N2 to a peak airway pressure of 30 cm H2O. QLPA was measured before and 5 minutes after LMBO.

Infusion of angiotensin II. Increasing doses of angiotensin II (0.05, 0.5, and 5.0 ng/g bw per minute) dissolved in sterile normal saline were infused via the central venous catheter using an infusion pump (Pump 11; Harvard Apparatus Co., South Natick, Mass.). PLA, PPA, PSA, and QLTAF were continuously measured.

Breathing with supplemental NO. Mice were housed in specially constructed chambers (Steudel et al., supra) where they breathed spontaneously for 22 hours at an inspired oxygen fraction ($FiO_2$) of 0.21 with 40 ppm NO added to the inspiratory gas mixture. After exposure, mice were removed from the chambers and breathed air during the induction of anesthesia. Hemodynamic measurements were obtained 60 minutes after removal from the chambers. During measurements, animals were mechanically ventilated at $FiO_2$ 1.0 without supplemental NO.

Validation of pulmonary blood flow measurements. In saline-treated wild-type mice (n=5), we compared simultaneous measurements of fractional pulmonary blood flow distribution made using intravenous injections of fluorescent-labeled microspheres (Glenny et al., 1993, J. Appl. Physiol. 74:2585–2597) with those made using ultrasonic flow probes, as already described here. Before LMBO, 50,000 colored microspheres (15-$\mu$m NuFlow Spheres; Interactive Medical Technologies Ltd., West Los Angeles, Cailf.), suspended in 0.2 mL saline containing 0.05% Tween-80 surfactant to prevent aggregation, were vortexed and then immediately infused (over 30 seconds) through a jugular vein cannula. After completion of the injection, the catheter was flushed with 0.1 mL saline. After 5 minutes of LMBO, microsphere injection was repeated using microspheres of a different color. Animals were sacrificed, and the lungs were harvested and weighed separately. Tissue samples were analyzed for total microsphere counts using flow cytometric analysis. The fraction of pulmonary blood flow to the right or left lung was calculated as total spheres to right or left lung over total spheres in both lungs.

In additional saline-treated wild-type mice (n=6), to confirm that the LMBO-induced redistribution of pulmonary blood flow was reflected by an increase in left pulmonary vascular resistance, we directly measured QLPA during transient occlusion of the inferior vena cava and calculated the slope and intercept of the left pulmonary artery pressure-flow relationship.

Lung wet/dry ratio. After euthanasia with pentobarbital (0.1 mg/g intraperitoneally), both lungs, excluding hilar structures, were excised, blotted, and immediately weighed. Thereafter, the tissue was dried in a microwave oven for 60 minutes, as described previously (20), and reweighed. Lung wet/dry ratio was calculated.

Statistical analysis. Changes of pulmonary blood flow are expressed as the percent reduction of baseline blood flow. Differences between groups were determined using a 2-way ANOVA. When significant differences were detected by ANOVA, a post hoc Fisher's test was used (Statistica for Windows; StatSoft Inc., Tulsa, Okla.). A P value of less than 0.05 indicated a significant difference. All data are expressed as mean±SEM.

Results

Figures 9A, 9B, 9C:
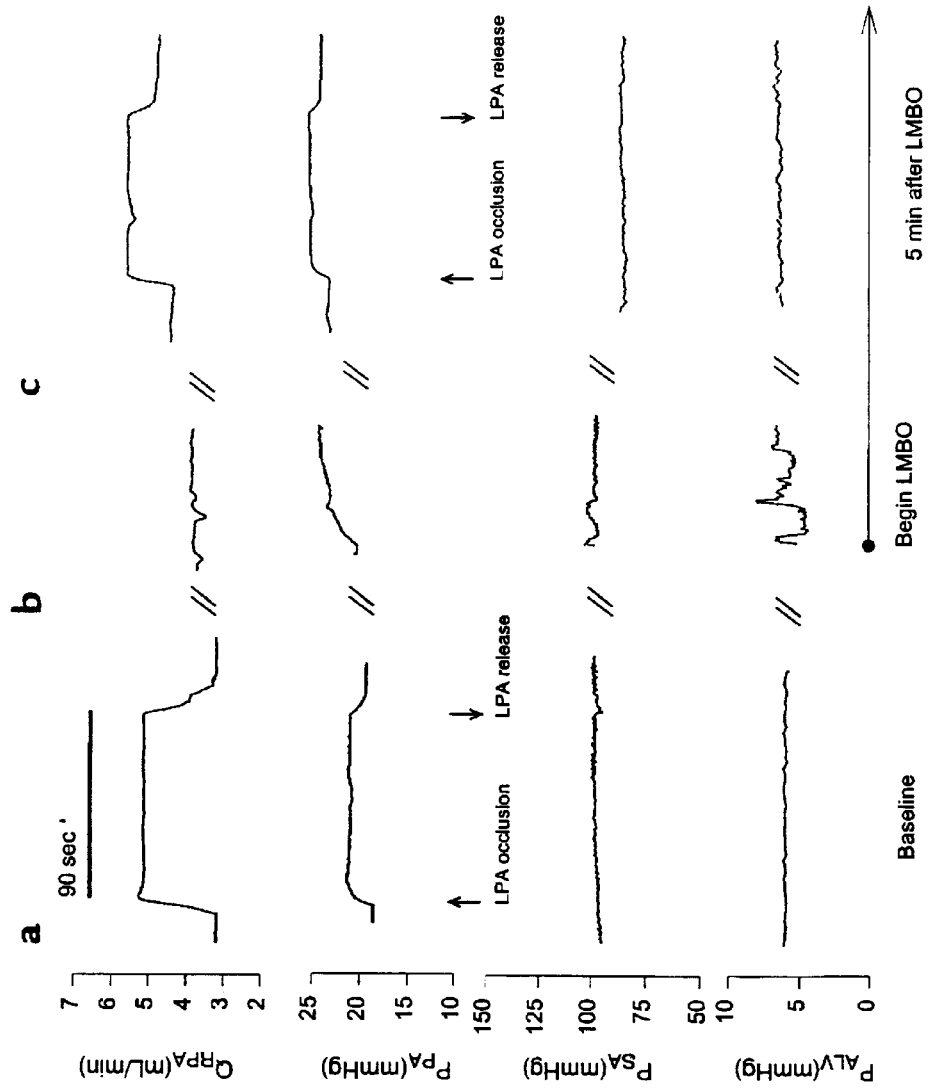
FIGS. 9A–9C are representative tracings of pulmonary and systemic hemodynamic measurements before and during LMBO with and without transient left pulmonary artery (LPA) occlusion. Effects of unilateral alveolar hypoxia induced by LMBO on central hemodynamics before (a) and during LMBO (b and c) are portrayed. Total alveolar collapse occurred about 1 minute after LMBO. Continuous recordings of mean flow through the right pulmonary artery (QRPA), mean pulmonary artery pressure (PPA), mean systemic arterial pressure (PSA), and mean airway pressure (PALV) in a saline-treated wild-type mouse at baseline and after LMBO. To assess blood flow distribution between the right and left pulmonary arteries, the left pulmonary artery was transiently occluded, at which point QRPA=QPA (see a and c). The difference of QPA−QRPA equals QLPA. Measurements were taken at baseline and 5 minutes after LMBO. Arrows indicate occlusion (90 seconds) and release of the left pulmonary artery.

Effects of unilateral alveolar hypoxia on pulmonary blood flow. To assess HPV in vivo, we developed a murine model in which differential pulmonary blood flow measurements could be obtained before and during left lung unilateral alveolar hypoxia (FIGS. 9A–9C). Because occlusion of the right mainstem bronchus caused severe hypoxemia and hemodynamic instability, we elected to occlude the left mainstem bronchus (LMBO), which produced a stable model of unilateral lung collapse. Differential pulmonary blood flow was measured at thoracotomy using an ultrasonic flow probe placed around the right pulmonary artery, and the flow distribution between the right and left lung was assessed by transiently occluding the left pulmonary artery (FIGS. 9A–9C).

FIGS. 9A–9C show representative tracings of pulmonary and systemic hemodynamic measurements before (FIG. 9A), at the initiation of LMBO (FIG. 9B), and 5 minutes after LMBO (FIG. 9C) with and without transient left pulmonary artery (LPA) occlusion. Transient occlusion of left pulmonary artery flow did not produce any systemic hemodynamic effect (FIG. 9A). Total lung collapse occurred about 1 minute after LMBO.

Online recordings of mean flow through the right pulmonary artery ($Q_{RPA}$), mean pulmonary artery pressure ($P_{PA}$), mean systemic arterial pressure ($P_{SA}$), and mean airway pressure ($P_{ALV}$) in a saline-treated wild-type mouse at baseline and after LMBO are presented. To assess blood flow distribution between right and left pulmonary arteries, the left pulmonary artery was transiently occluded, at which point $Q_{RPA}=Q_{PA}$ (see FIG. 9A and FIG. 9C). The difference of $Q_{PA}$ and $Q_{RPA}$ equals $Q_{LPA}$. Measurements were taken at baseline and 5 minutes after LMBO. Arrows indicate occlusion (90 seconds) and release of left pulmonary artery. These representative tracings highlight the ability to measure pulmonary blood flow distribution in vivo in the mouse.

Figure 10A:
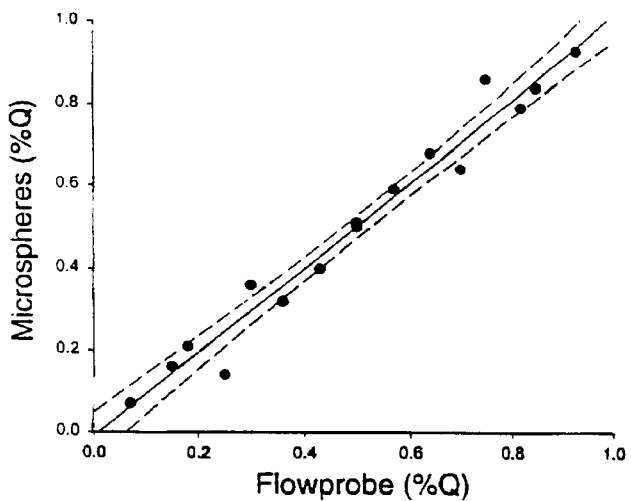
FIG. 10A is a graph showing correlation of percent pulmonary blood flow to the left or right lung assessed by intravenous injection of fluorescent microspheres (15 μm dia.) and by simultaneous measurement of QRPA with an ultrasonic flow probe. Values are expressed as the fractional flow to the right or left lung before and after LMBO (saline-treated wild-type mice; n=4). Note the close agreement between the 2 methods (r2=0.967).
Figure 10B:
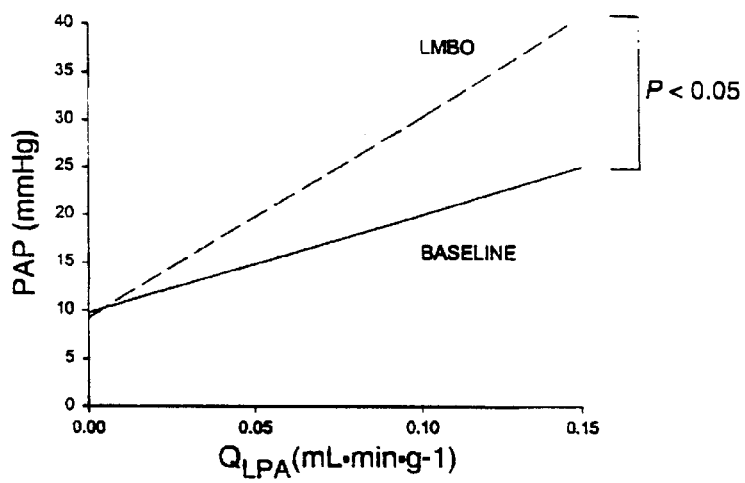
FIG. 10B is a graph showing results of experiments on the left lung pulmonary flow-pressure relationship before (baseline) and after 5 minutes of LMBO in saline-treated wild-type mice (n=6). Left pulmonary artery flow (QLPA) was measured by an ultrasonic flow probe, and the slopes were generated by reducing QPA with a transient occlusion of the inferior vena cava (P<0.05, slope differs versus baseline).
Figure 10C:
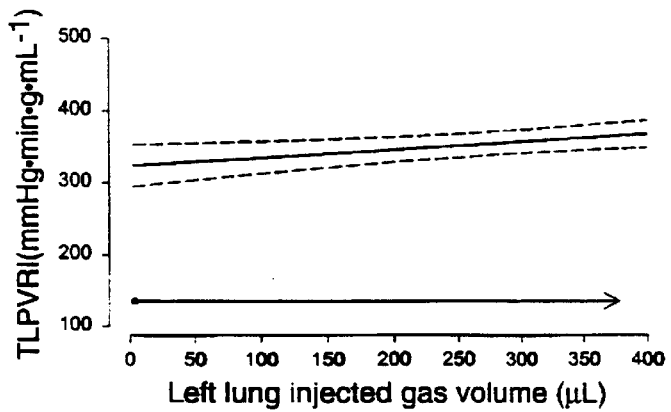
FIG. 10C is a graph illustrating changes in total left lung pulmonary vascular resistance (TLPVR) during re-expansion of the collapsed left lung in saline-treated wild-type mice (n=3). Values are expressed as a linear regression of all data points with the respective 95% confidence intervals.

FIGS. 10A–10C show the experimental approaches used to validate the method of measuring pulmonary blood flow distribution in the mouse. FIG. 10A shows the correlation of percent pulmonary blood flow to the left or right lung assessed by intravenous injection of fluorescent microspheres (15 $\mu$m in diameter) and by simultaneous measurement of $Q_{RPA}$ with an ultrasonic flow probe. In the latter method, differential blood flow distribution between the right and left pulmonary artery was assessed by transient occlusion of the left pulmonary artery. Values are expressed as the fractional flow to the right or left lung before and after LMBO (saline-treated wild-type mice; n=4). Note the close agreement between the 2 methods ($r^2$=0.967). FIG. 10B shows results of experiments on the left lung pulmonary flow-pressure relationship before (baseline) and after 5 minutes of LMBO in saline-treated wild-type mice (n=6). Note the significant increase of the slope, which represents an increased incremental left lung pulmonary vascular resistance induced by LMBO. In these studies, left pulmonary artery flow ($Q_{LPA}$) was measured directly using an ultrasonic flow probe, and the slopes were generated by reducing $Q_{PA}$ with a transient occlusion of the inferior vena cava (P<0.05, slope differs versus baseline). FIG. 10C illustrates changes in total left lung pulmonary vascular resistance (TLPVR) during re-expansion of the collapsed left lung in saline-treated wild-type mice (n=3). The left lung was inflated by a continuous injection of 5% $CO_2$ in $N_2$ up to a peak inspiratory pressure of 30 cm $H_2O$. Values are expressed as a linear regression of all data points with the respective 95% confidence intervals. These results demonstrated that the redistribution of pulmonary blood flow after LMBO is attributable to hypoxia and not to left lung collapse.

Before LMBO, hemodynamic parameters did not differ between wild-type mice and NOS2-deficient mice. Five minutes after LMBO, QLPA/QPA was reduced by 46±5% in saline-treated wild-type mice and by 50±7% in saline-treated NOS2-deficient mice (FIG. 7). In supplemental studies in which QLPA was measured directly using a flow probe around the left pulmonary artery, we observed that the LMBO-induced pulmonary blood flow redistribution was reflected by an increase in incremental left pulmonary vascular resistance from 102±18 mmHg•min•g•mL$^{-1}$ to 210±38 mmHg•min•g•mL$^{-1}$ (FIG. 10B). LMBO-induced pulmonary blood flow redistribution was not attributable to mechanical factors associated with left lung collapse, as left pulmonary vascular resistance (LPVR) did not change when the collapsed lung was reinflated to a normal lung volume under direct vision with 5% $CO_2$ in N2 (n=3; FIG. 10C).

Effect of endotoxemia on pulmonary and systemic hemodynamics during unilateral alveolar hypoxia. After challenge with intraperitoneal injection of 10 mg/kg $E.$ $coli$ endotoxin, mice appeared lethargic with piloerection and diarrhea. Approximately 50% of mice died within 1 week after endotoxin challenge, and there were no differences in mortality between wild-type and NOS2-deficient mice (data not shown). Before LMBO, hemodynamic parameters did not differ between saline-treated mice and endotoxin-treated mice (FIG. 12), but QPA tended to be higher in endotoxin-treated wild-type mice than in NOS2-deficient mice (230±35 vs. 120±32 $\mu$L•min$^{-1}$•g$^{-1}$ bw), although this difference did not reach statistical significance. Comparison of QPA for all studied endotoxin-challenged wild-type and NOS2-deficient mice confirmed that there was no difference between the two genotypes (wild-type mice 180±20 $\mu$L/min per gram; NOS2-deficient mice 140±15 $\mu$L/min per gram; n=21 and 15, respectively). Because differences in QPA potentially affect pulmonary blood flow redistribution, we tested whether changes in QLPA/QPA depended on changes in QPA. Linear regression analysis revealed no correlation between QPA and QLPA/QPA during LMBO ($r^2$=0.03, both for all mice and for all endotoxin-treated mice (P<0.001; FIG. 7). After LMBO, the QLPA/QPA was reduced by 46±5% in saline treated wild type mice, and by 18±5% in endotoxin treated wild type mice. In contrast, LMBO reduced QLPA/QPA by 50±7% in saline-treated NOS2-deficient mice and by 51±6% in endotoxin-treated NOS2-deficient mice (FIG. 7). There was no difference in the response to endotoxin between SV129, SV129B6F1, or C57BL/6 wild-type strains or between NOS2-deficient mice with SV129/B6F1-hybrid background and NOS2-deficient mice backcrossed for 10 generations on a C57BL/6 background (data not shown).

Figure 11:
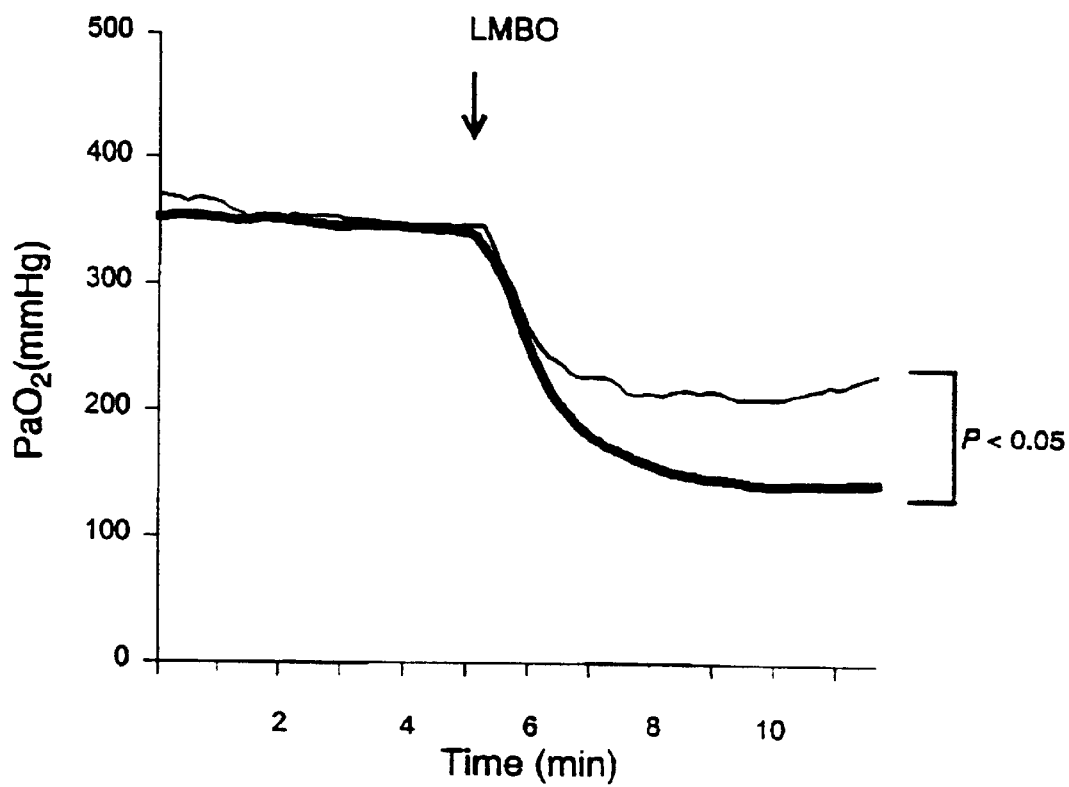
FIG. 11 is a graph showing effects of regional hypoxia induced by LMBO on the systemic arterial partial pressure of oxygen ($PaO_2$) in endotoxin-treated wild-type mice (thick line) and endotoxin-treated NOS2-deficient mice (narrow line). Endotoxin was administered 22 hours before study by an intraperitoneal injection of 10 mg/kg E. coli endotoxin. Continuous recordings of $PaO_2$ were obtained with a Clark-type oxygen electrode located in the aortic arch. Data are the mean of independent experiments with wild-type mice (n=5) and NOS2-deficient mice (n=3).

Effect of endotoxemia on $PaO_2$ and $PvO_2$ during unilateral alveolar hypoxia. To determine whether the differences in LMBO-induced pulmonary blood flow redistribution noted in wild-type and NOS2-deficient mice after endotoxin challenge are reflected by differences in LMBO-induced changes in arterial oxygenation, the $PaO_2$ was continuously measured before and during LMBO. In separate endotoxin-treated wild-type and NOS2-deficient mice, the effect of LMBO on $PvO_2$ was also assessed. In saline-treated wild-type mice (n=4), breathing at $FiO_2$ 1.0, LMBO for 5 minutes decreased the $PaO_2$ from 432±7 mmHg to 225±13 mmHg. The $PaO_2$ was 342±23 mmHg in endotoxin-treated wild-type mice and 347±33 mmHg in endotoxin-treated NOS2-deficient mice. After 5 minutes of LMBO, the $PaO_2$ decreased more in endotoxin-treated wild-type mice (145±9 mmHg) than in endotoxin-treated NOS2-deficient mice (230±18 mmHg; P<0.05; FIG. 11).

$PvO_2$ did not differ in endotoxin-treated wild-type mice and endotoxin-treated NOS2-deficient mice (before LMBO: 39±5 and 44±8 mmHg, respectively; after LMBO: 34±4 and 43±7 mmHg, respectively; n=3 for both groups).

Prolonged Pharmacologic Inhibition of NOS2 Activity. To determine whether prolonged pharmacologic inhibition of NOS2 preserves HPV, wild-type mice (n=5) were injected intraperitoneally with 10 mg/kg endotoxin, and 3 hours later were treated with L-NIL (5 mg/kg intraperitoneally), a selective inhibitor of NOS2 activity. This dose of L-NIL was sufficient to prevent the increase in pulmonary cGMP levels in wild-type mice 7 hours after endotoxin challenge (data not shown). Pulmonary blood flow studies were performed 22 hours after the endotoxin challenge. In endotoxin-exposed mice treated with L-NIL, we measured no differences in systemic and pulmonary hemodynamics before LMBO, compared with saline-treated or endotoxin-treated wild-type mice. The reduction of QLPA/QPA was greater in endotoxin-challenged wild-type mice treated with L-NIL than in wild-type mice receiving endotoxin alone (53±10% vs. 18±5%, respectively; P<0.01; FIG. 7).

Acute pharmacologic inhibition of NOS2 with L-NIL. To determine whether acute inhibition of NOS2 enzyme activity augmented HPV during LMBO, pulmonary blood flow studies were performed in saline-treated and endotoxin-treated wild-type mice during which L-NIL (5 mg/kg intravenously) was administered after LMBO. In saline-treated wild-type mice (n=5), acute L-NIL administration did not further reduce QLPA/QPA during LMBO (49±3% before L-NIL; 56±3% after L-NIL). All other hemodynamic parameters did not change after L-NIL injection. In wild-type mice treated with endotoxin 22 hours earlier (n=4), acute L-NIL administration did not further reduce QLPA/

QPA during LMBO (22±11% reduction before L-NIL; 24±18% reduction after L-NIL).

Prolonged inhalation of 4 or 40 ppm NO. To learn whether increased pulmonary levels of NO, rather than another NOS2 product, contribute to the endotoxin-induced impairment of HPV, saline-treated and endotoxin-challenged wild-type and NOS2-deficient mice breathed 40 ppm NO in air for 22 hours. The hemodynamic studies were performed 1 hour later, allowing ample time for any potential vasodilator action of inhaled NO to dissipate. Inhalation of 40 ppm NO for 22 hours did not impair HPV in saline-treated wild-type mice and NOS2-deficient mice: reduction of QLPA/QPA after LMBO was 51±10% in saline-treated wild-type mice and 50±11% in saline-treated NOS2-deficient mice after breathing 40 ppm NO for 22 hours (FIG. 7). Except for a modest difference in heart rate, no other differences in pre-LMBO hemodynamics were found between endotoxin-treated and saline-treated mice exposed to prolonged inhalation of 40 ppm NO for 22 hours (FIG. 12). After prolonged inhalation of 40 ppm NO, endotoxin-treated NOS2-deficient mice demonstrated a marked attenuation of HPV compared with endotoxin-treated NOS2-deficient mice that did not breathe supplemental NO (reduction of QLPA/QPA: 20±7% vs. 50±11%, respectively; P<0.05; FIG. 7). In contrast, prolonged NO inhalation did not affect the endotoxin-induced impairment of HPV in wild-type mice (reduction of QLPA/QPA: 19±10% in endotoxin-treated wild-type mice breathing 40 ppm NO for 22 hours versus 18±5% in endotoxin-treated wild-type mice not exposed to NO; FIG. 7). In contrast, breathing 4 ppm NO for 22 hours did not impair HPV in endotoxin-treated NOS2-deficient mice (reduction of QLPA/QPA: 62±2%; n=4).

Pulmonary vasoreactivity to angiotensin II. To determine whether the impact of endotoxin on HPV was attributable to a nonspecific effect of endotoxin on pulmonary vascular contractile function, we measured the pulmonary vasoconstrictor response to increasing intravenous doses of angiotensin II in saline-treated wild-type mice and wild-type mice 22 hours after endotoxin challenge. PVR increased from 74±24 at baseline to 184±25 mmHg•min•g•mL-1 at 5.0 µg/kg per minute angiotensin II in saline-treated wild-type mice without endotoxin (P<0.01) and from 55±11 to 174±40 mmHg•min•g•mL$^{-1}$ in endotoxin-challenged wild-type mice (P<0.001). At any angiotensin II infusion dose level, there was no difference in the PVR of endotoxin-treated and saline-treated mice. PLA at baseline did not differ between saline-treated wild-type mice (6±1 mmHg) and endotoxin-treated wild-type mice (5±1 mmHg), and PLA did not change in response to angiotensin II infusion in either group.

Lung wet/dry weight ratios. Wet/dry lung weight ratios did not differ between endotoxin-challenged wild-type (wet weight/dry weight: 5.0±0.5) and NOS2-deficient mice (4.6±0.2), or saline-treated wild-type (4.6±0.1) and saline-treated NOS2-deficient mice (4.5±0.1). Breathing 4 or 40 ppm NO for 22 hours did not alter the wet/dry lung weight ratios.

Summary and Interpretation of Experiments. To investigate the role of NO and NOS2 in the impairment of HPV in sepsis, we developed an in vivo mouse model to assess the redistribution of pulmonary blood flow in response to unilateral alveolar hypoxia produced by LMBO. In mice not exposed to endotoxin, LMBO doubled left lung PVR, thereby diverting 50% of left pulmonary blood flow to the right lung and causing a modest decrease in PaO$_2$. Changes in murine pulmonary blood flow distribution measured using ultrasonic flow probes at thoracotomy were closely correlated with measurements obtained using intravenous injection of fluorescent microspheres (see FIG. 10A) and were similar to those reported by investigators studying large animal models (Domino et al., 1984, *Anesthesiology* 60:562–566; Sprague et al., 1992, *Proc. Natl. Acad. Sci. USA* 89:8711–8715).

In wild-type mice 22 hours after an endotoxin challenge, we observed that the ability to redistribute pulmonary blood flow in response to regional lung hypoxia was severely impaired, leading to a marked deterioration in systemic arterial oxygenation. This endotoxin-induced impairment of pulmonary blood flow redistribution in the mouse is similar to that observed in awake sheep after intravenous challenge with live bacteria (Fischer, et al., 1997, *Am. J. Respir. Crit. Care Med.* 156:833–839) or endotoxin (Hutchison et al., 1985, *J. Appl. Physiol.* 58:1463–1468).

It did not appear that the endotoxin-induced impairment of HPV was due to nonspecific dysfunction of the vasomotor contractile apparatus because we found that the ability of angiotensin II to vasoconstrict the pulmonary vasculature did not differ in endotoxin-challenged and saline-treated mice. Moreover, the deleterious effect of endotoxin on the murine pulmonary vasculature was reversible with restoration of HPV at 14 days after endotoxin administration (data not shown).

In NOS2-deficient mice challenged with endotoxin 22 hours earlier, HPV was not impaired and there was preservation of systemic arterial oxygenation during LMBO. Similarly, HPV was preserved in wild-type mice treated with L-NIL, a specific inhibitor of NOS2 enzyme activity, 3 hours after endotoxin challenge. These results demonstrate that NOS2 enzyme activity is critical to produce the endotoxin-induced impairment of HPV.

It is unlikely that impairment of HPV in wild-type mice 22 hours after endotoxin challenge is attributable to excess pulmonary NO levels, as acute administration of L-NIL immediately after LMBO did not restore HPV. These results demonstrate that endotoxin-induced pulmonary NOS2 expression is necessary to impair HPV but that continued NOS2 activity is not required for the impairment of HPV measured 22 hours after the endotoxin challenge.

Under certain conditions, NOS2 can produce superoxide, as well as NO (28). We examined whether NO produced by NOS2 contributed to the endotoxin-induced impairment of HPV by replenishing pulmonary NO levels via inhalation in endotoxin-challenged NOS2-deficient mice. NOS2-deficient mice were challenged with endotoxin and placed in an exposure chamber containing varying concentrations of NO for 22 hours. Pulmonary blood flow redistribution in response to LMBO was measured 1 hour after removal from the chamber, by which time pulmonary NO levels would not be expected to be elevated. HPV was impaired in endotoxin-challenged NOS2-deficient mice that breathed 40 ppm NO (see FIG. 7). In contrast, breathing 4 ppm NO for 22 hours did not impair HPV in endotoxin-treated NOS2-deficient mice. These data suggest that markedly elevated pulmonary NO levels (either produced endogenously by NOS2 or inhaled) are required to impair HPV. If our observations in mice are extrapolated to human beings, an important clinical implication of our studies is that the administration of high concentrations of inhaled NO to patients with pulmonary inflammation may attenuate HPV, leading to a paradoxical decrease in arterial oxygenation. Moreover, these findings support the current clinical practice of using the lowest effective concentration of inhaled NO when treating patients with acute respiratory failure (Zapol, 1993, *Intensive Care Med.* 19:433–434).

In saline-treated wild-type and NOS2-deficient mice, inhalation of 40 ppm NO for 22 hours did not impair HPV when the animals were studied 1 hour after removal from the exposure chamber (see FIG. 7). These results suggest that sustained increases in pulmonary NO levels alone are insufficient to cause lasting impairment of HPV. In addition, breathing 40 ppm NO for 22 hours did not further impair HPV in endotoxin-challenged wild-type mice. Thus, it appears that inhaled NO and endotoxin-induced pulmonary NO production are not additive with respect to impairing HPV. Our studies suggest that the lasting impairment of HPV after endotoxin challenge requires both increased pulmonary NO levels and additional endotoxin-induced inflammatory products.

EXAMPLE 3

Leukotriene Blockers and Impairment of HPV

Experimental evidence was obtained demonstrating that inhibitors of leukotriene synthesis and inhibitors of leukotriene receptor activation prevent the impairment of HPV in endotoxin-challenged mice. We found that HPV is preserved in endotoxin-challenged mice deficient in 5-lipoxygenase (5LO), which catalyzes conversion of arachidonic acid into leukotriene A4, when 5LO-activating protein (FLAP) is present. We found that in wild-type mice, HPV is preserved in endotoxin-challenged mice treated with FLAP inhibitor MK886, or CysT1 receptor blocker MK571. For these experiments, we used an in vivo mouse model of one-lung hypoxia.

Wild-type (SV129B6/F1) mice and 5LO-deficient mice were anesthetized and studied at thoracotomy. Left pulmonary artery flow (QLPA) and pulmonary (PPA) and systemic (PSA) artery pressures were measured continuously. Pressure flow relationships for the left pulmonary circulation were obtained by transient occlusion of the inferior vena cava.

Figure 13:
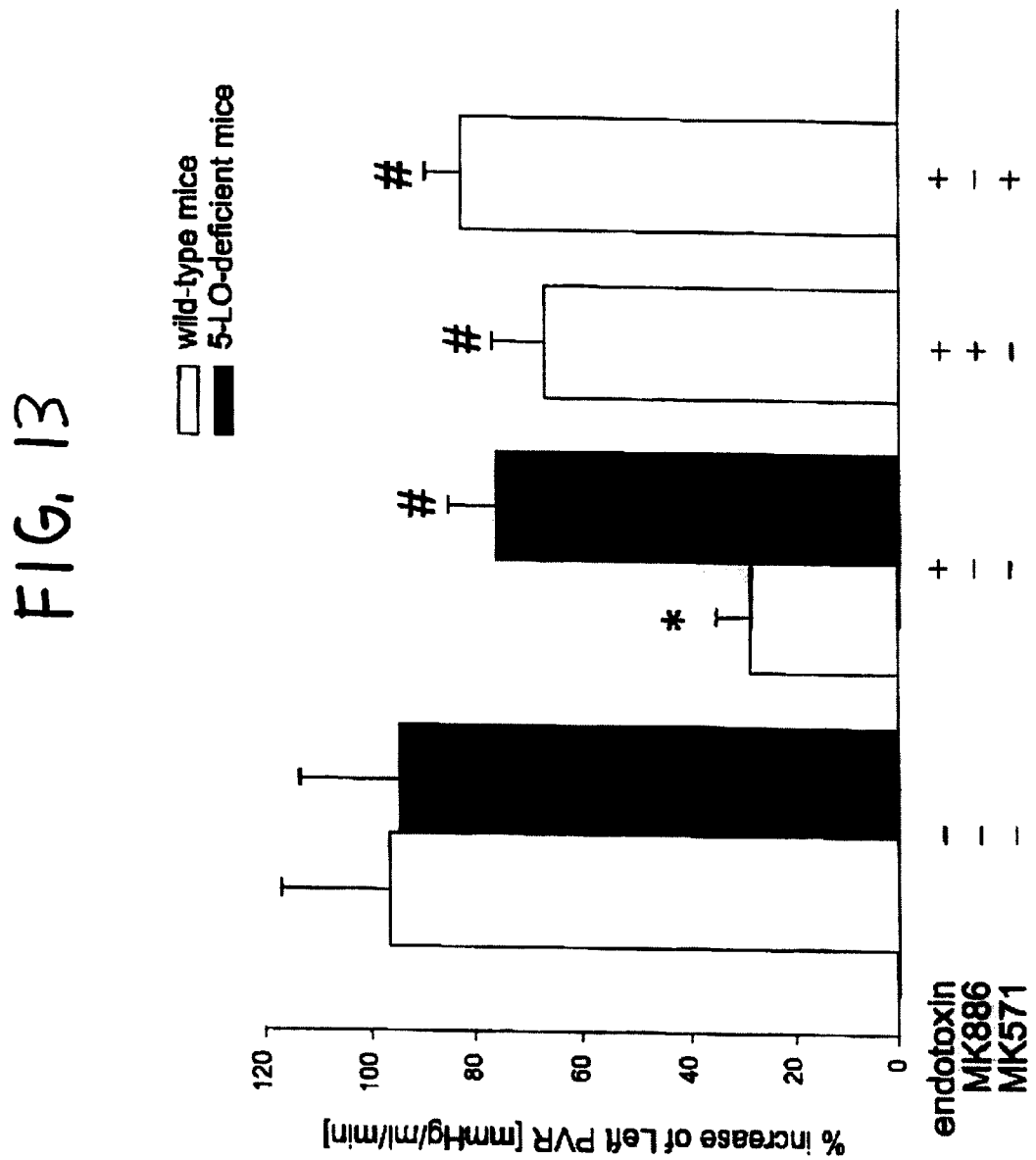
FIG. 13 is a histogram summarizing data from experiments on the LMBO-induced increase in left lung pulmonary vascular resistance (left PVR) in saline-challenged wild-type mice (n=7), saline-challenged 5-LO-deficient (n=7) mice, endotoxin-challenged wild-type mice (n=8), endotoxin-challenged 5LO-deficient (n=9) mice, endotoxin-challenged wild-type mice treated with the 5-LO-activating protein inhibitor, MK886 (n=8), and endotoxin-challenged wild-type mice treated with a $cysLT_1$-receptor antagonist, MK571 (n=7). *P<0.01 vs. saline-challenged wild-type mice; #P<0.01 vs. endotoxin-challenged wild-type mice.

HPV was assessed as the percent increase in left pulmonary vascular resistance (the slope of the P/Q-relationship, LPVR) after left main bronchus occlusion (LMBO). LMBO increased LPVR by 99±13% in 5LO deficient mice, and by 100±11% in wild-type mice. Data are summarized in FIG. 13. These results demonstrated that inhibition of cysteinyl-leukotriene synthesis or receptor activation prevented the endotoxin-induced impairment of HPV.

OTHER EMBODIMENTS

A number of embodiments of the invention have been described. Nevertheless, it will be understood that various modifications may be made without departing from the spirit and scope of the invention. For example, the invention can be practiced using anti-ROS agents and leukotriene blockers other than the ones listed herein. Accordingly, other embodiments are within the scope of the following claims.

What is claimed is:

1. A method for reducing, partially preventing or completely preventing nitric oxide inhalation-related impairment of hypoxic pulmonary vasoconstriction in a mammal, comprising: administering to the mammal a therapeutically effective amount of nitric oxide by inhalation, and co-administering an amount of at least one anti-reactive oxygen species (anti-ROS) agent effective to reduce, partially prevent or completely prevent nitric oxide inhalation-related impairment of hypoxic pulmonary vasoconstriction in the mammal.

2. The method of claim 1, wherein the anti-ROS agent is selected from the group consisting of: allopurinol, bilirubin, caffeic acid, catalase, PEG-catalase, catechin, ceruloplasm, copper diisopropylsalicylate, deferoxamine mesylate, dimethylurea, ebselen, EUK-8, FeTMTPyP, FETPPS, glutathione, MnTBAP, MnTMPyP, selenomethionine, superoxide dismutase, PEG-superoxide dismutase, and dihydroquercetin.

3. The method of claim 1, wherein the anti-ROS agent is N-acetylcysteine.

4. The method of claim 1, further comprising co-administering an effective amount of a leukotriene blocker.

5. The method of claim 4, wherein the leukotriene blocker is prankulast, MK-571, MK-591, MK-886, BAYx1005, cinalukast, pobilukast edamine, MK-679, or ZD2138.

6. The method of claim 4, wherein the leukotriene blocker is montelukast, zafirlukast.

7. The method of claim 1, wherein the mammal has acute pulmonary injury.

8. The method of claim 1, wherein the mammal has acute respiratory distress syndrome.

9. The method of claim 1, wherein the mammal has diffuse pulmonary infection.

10. The method of claim 1, wherein the mammal has sepsis.

11. The method of claim 1, wherein the mammal has lung inflammation.

12. The method of claim 1, wherein the method comprises co-administering to the mammal two or more-different anti-ROS agents.

13. The method of claim 1, wherein the anti-ROS agent is administered to the mammal by inhalation.

14. The method of claim 1, wherein the anti-ROS agent is administered to the mammal by intravenous administration.

15. The method of claim 1, wherein the administration of the anti-ROS agent is commenced concurrently with initiation of nitric oxide inhalation.

16. The method of claim 1, wherein the anti-ROS agent is a scavenger of peroxynitrite.

17. The method of claim 1, wherein the anti-ROS agent is a glucocorticod.

18. The method of claim 1, wherein the anti-ROS agent is ascorbic acid (vitamin C) or vitamin E.

19. A method for reducing, partially preventing or completely preventing loss of pulmonary vasodilatory responsiveness to nitric oxide inhalation in a mammal, comprising: administering to the mammal a therapeutically effective amount of nitric oxide by inhalation, and co-administering an amount of at least one anti-ROS agent effective to reduce, partially prevent or completely prevent loss of pulmonary vasodilatory responsiveness to nitric oxide inhalation in the mammal.

20. The method of claim 19, wherein the anti-ROS agent is selected from the group consisting of: allopurinol, bilirubin, caffeic acid, catalase, PEG-catalase, catechin, ceruloplasm, copper diisopropylsalicylate, deferoxamine mesylate, dimethylurea, ebselen, EUK-8, FeTMTPyP, FETPPS, glutathione, MnTBAP, MnTMPyP, selenomethionine, superoxide dismutase, PEG-superoxide dismutase, and dihydroquercetin.

21. The method of claim 19, wherein the anti-ROS agent is N-acetylcysteine.

22. The method of claim 19, further comprising co-administering an effective amount of a leukotriene blocker.

23. The method of claim 22, wherein the leukotriene blocker is prankulast, MK-571, MK-591, MK-886, BAYx1005, cinalukast, pobilukast edamine, MK-679, or ZD2138.

24. The method of claim wherein the leukotriene blocker is montelukast, zafirlukast, or zileuton.

25. The method of claim 19, wherein the mammal has acute pulmonary injury.

26. The method of claim 19, wherein them acute respiratory distress syndrome.

27. The method of claim 19, wherein the mammal has diffuse pulmonary infection.

28. The method of claim 19, wherein the mammal has sepsis.

29. The method of claim 19, herein the mammal has lung inflammation.

30. The method of claim 19, wherein the method comprises co-administering to the mammal two or more, different-anti ROS agents.

31. The method of claim 19, wherein the anti-ROS agent is administered to the mammal by inhalation.

32. The method of claim 19, wherein the anti-ROS agent is administered to the mammal by intravenous administration.

33. The method of claim 19, wherein the administration of the anti-ROS agent is commenced concurrently with initiation of nitric oxide inhalation.

34. The method of claim 19, wherein the anti-ROS agent is a scavenger of peroxynitrite.

35. The method of claim 19, wherein the anti-ROS agent is a glucocorticoid.

36. The method of claim 19, wherein the anti-ROS agent is ascorbic acid (vitamin C) or vitamin E.

* * * * *

UNITED STATES PATENT AND TRADEMARK OFFICE
CERTIFICATE OF CORRECTION

PATENT NO. : 6,601,580 B1
DATED : August 5, 2003
INVENTOR(S) : Kenneth D. Bloch, Fumito Ichinose and Warren M. Zapol It is certified that error appears in the above-identified patent and that said Letters Patent is hereby corrected as shown below:

Title page,
Item [56], References Cited, OTHER PUBLICATIONS, "Charleson et al.," replace "Requirements" with -- Requirements --; and
"Hatzelmann et al.," reference, replace "Gay" with -- Bay --

Column 24,
Line 15, after "zafirlukast" insert -- , or zileuton --
Line 39, replace "glucocorticod" with -- glucocorticoid --

Column 25,
Line 1, after "claim" insert -- 22, --
Line 5, replace "them" with -- the mammal has --
Line 14, delete "," after "more"
Line 15, delete "-" after "different"

Signed and Sealed this

Twentieth Day of July, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,601,580 B1  Page 1 of 1
APPLICATION NO. : 09/605900
DATED : August 5, 2003
INVENTOR(S) : Kenneth D. Bloch, Fumito Ichinose and Warren M. Zapol It is certified that error appears in the above-identified patent and that said Letters Patent is hereby corrected as shown below:

<u>Column 1</u>
Line 5, after the Title, insert
--STATEMENT AS TO FEDERALLY SPONSORED RESEARCH
This invention was made with Government support under Grant Nos. HL057172, HL042397, and HL055377 awarded by the National Institutes of Health. The Government has certain rights in this invention.--

Signed and Sealed this

Fourteenth Day of July, 2009

JOHN DOLL
*Acting Director of the United States Patent and Trademark Office*